(12) United States Patent
Nelson et al.

(10) Patent No.: US 11,730,717 B1
(45) Date of Patent: Aug. 22, 2023

(54) MELANIN-INSPIRED ANTIMICROBIAL

(71) Applicant: The Board of Regents for the Oklahoma Agricultural and Mechanical Colleges, Stillwater, OK (US)

(72) Inventors: Toby Larue Nelson, Stillwater, OK (US); Santosh Adhikari, Los Alamos, NM (US); Erika Lutter, Stillwater, OK (US); Karen Wozniak, Guthrie, OK (US)

(73) Assignee: The Board of Regents for the Oklahoma Agricultural and Mechanical Colleges, Stillwater, OK (US)

( * ) Notice: Subject to any disclaimer, the term of this patent is extended or adjusted under 35 U.S.C. 154(b) by 96 days.

(21) Appl. No.: 17/374,535

(22) Filed: Jul. 13, 2021

Related U.S. Application Data

(60) Provisional application No. 63/052,033, filed on Jul. 15, 2020.

(51) Int. Cl.
| | |
|---|---|
| *A61K 31/404* | (2006.01) |
| *A61K 31/04* | (2006.01) |
| *A61K 31/10* | (2006.01) |
| *A01N 43/38* | (2006.01) |
| *A61P 31/04* | (2006.01) |
| *A61P 31/10* | (2006.01) |

(52) U.S. Cl.
CPC ............ *A61K 31/404* (2013.01); *A01N 43/38* (2013.01); *A61P 31/04* (2018.01); *A61P 31/10* (2018.01)

(58) Field of Classification Search
CPC ...... A61K 31/404; A61K 31/04; A61K 31/10; A01N 43/38
See application file for complete search history.

(56) References Cited

U.S. PATENT DOCUMENTS

2017/0174825 A1\*  6/2017  Nelson .................... C09D 5/24

\* cited by examiner

*Primary Examiner* — Timothy R Rozof
(74) *Attorney, Agent, or Firm* — Fellers, Snider, Blankenship, Bailey & Tippens, P.C.; Terry L. Watt

(57) ABSTRACT

Herein, is taught a Eumelanin-inspired antimicrobial capable of overcoming methicillin resistant *Staphylococcus aureus* (MSRA) and *Enterococcus faecalis*. By ligating quaternary ammonium functionalized "arms" on to a Eumelanin-inspired indole, with intrinsic antimicrobial activity, a cell wall destroying antimicrobial agent was prepared. It also has antifungal effects against *Candida albicans*. Further, Eumelanin-inspired phenyleneethynylene (EIPE) derivatives EIPE-1 and EIPE-HCl are novel compounds. EIPE structure serves as scaffolding for functional groups that may have antibacterial properties. Both gram-positive and gram-negative organisms are screened against EIPE derivatives using a standardized Kirby Bauer disk agar diffusion assay. These results showed that EIPE-1 has antibacterial properties against some pathogenic gram-positive organisms.

19 Claims, 4 Drawing Sheets

 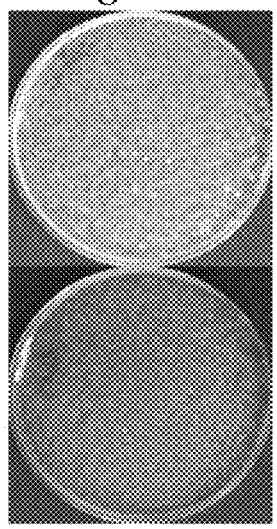 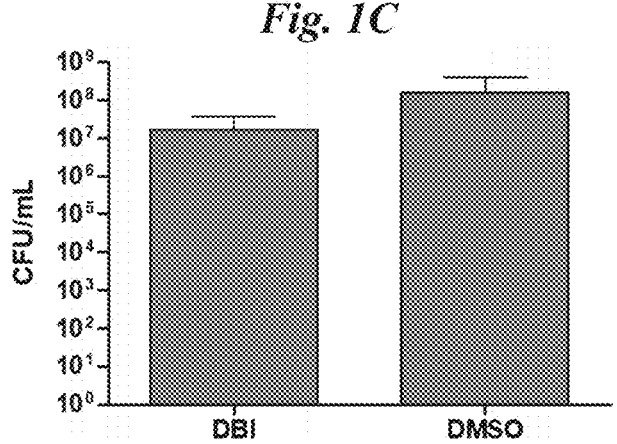
*Fig. 1A*  *Fig. 1B*  *Fig. 1C*
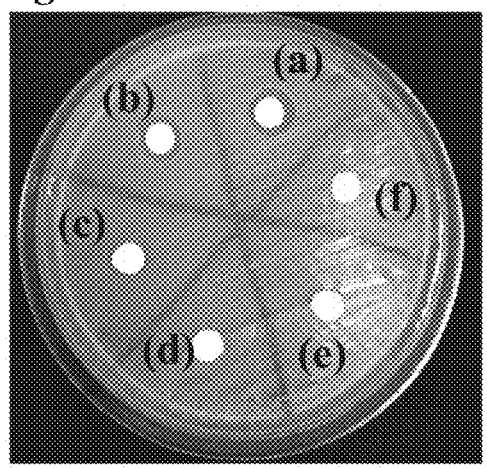 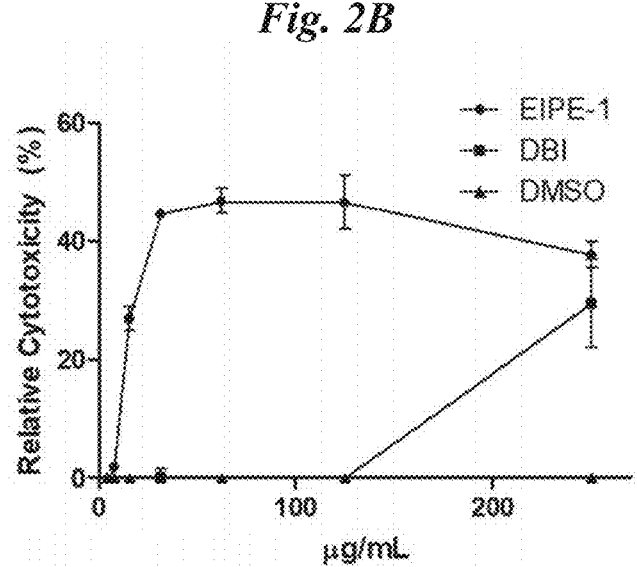
*Fig. 2A*  *Fig. 2B*
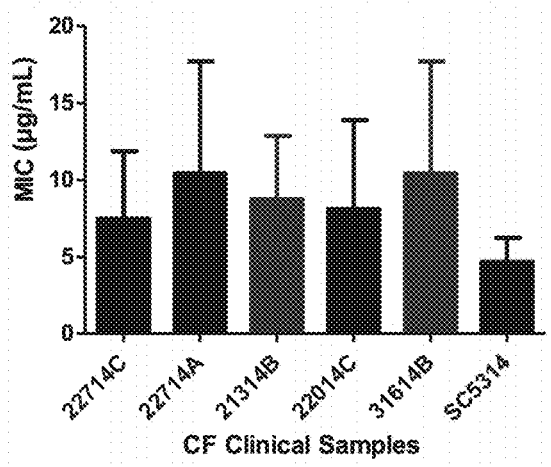
*Fig. 8*

*Fig. 6*
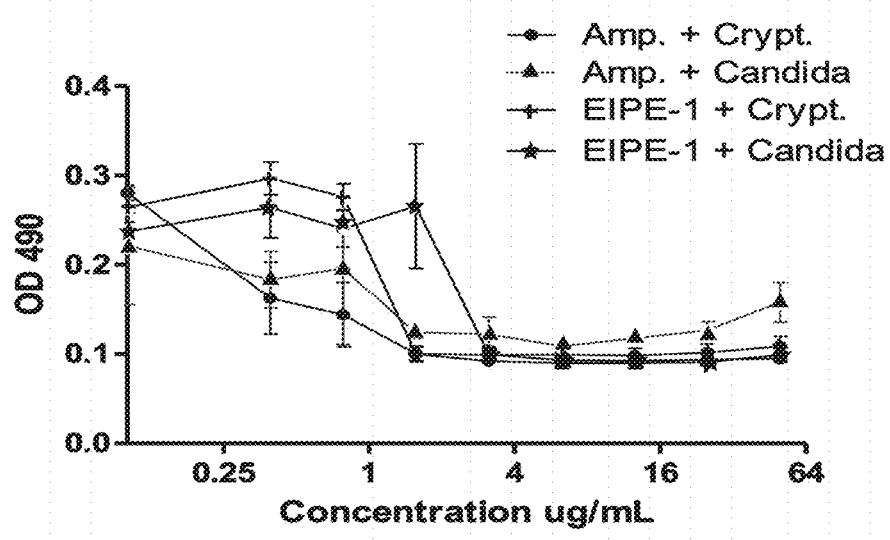
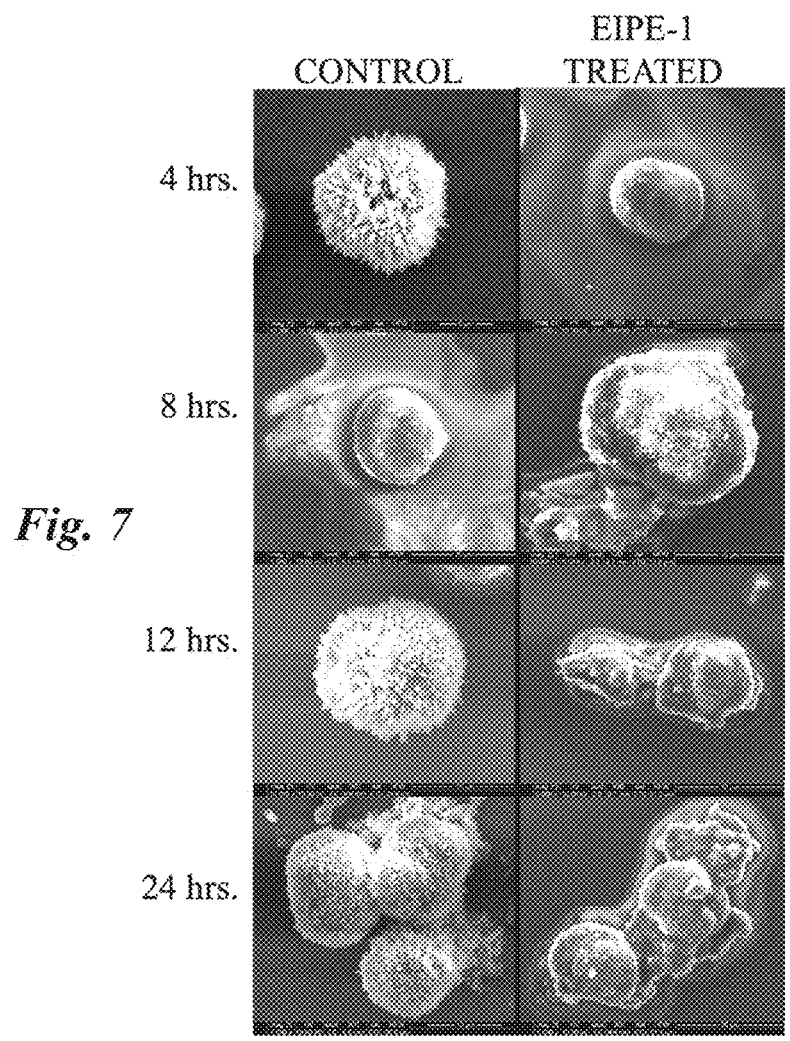
*Fig. 7*

MELANIN-INSPIRED ANTIMICROBIAL

CROSS REFERENCE TO RELATED APPLICATIONS

This application claims the benefit of U.S. Provisional Patent Application Ser. No. 63/052,033 filed on Jul. 15, 2020, and incorporates said provisional application by reference into this document as if fully set out at this point.

TECHNICAL FIELD

This disclosure relates generally to antibiotics useful against multi-drug resistant bacterial organisms and, more particularly, against *Staphylococcus aureus, Enterococcus faecalis*, etc., and to antifungal agents effective against *Candida albicans*, etc.

BACKGROUND

Bacterial antibiotic resistance is a serious worldwide threat which significantly impacts human health. As more pathogens gain resistance to antibiotics, standard treatments decrease in their efficacy, infections become more difficult or impossible to control, and the risk of spreading drug resistant infections greatly increases. Resistant pathogens have a major effect on patient morbidity and mortality as well as increased economic costs associated with treatments. Antibiotic resistance, due to misuse of drugs, has genetically selected for the survival of resistant bacterial strains which have rendered many clinically utilized antibiotics ineffective against drug-resistant bacteria, particularly methicillin resistant *Staphylococcus aureus* (MRSA). Much research has focused on creating and identifying novel antibiotics to combat drug resistant strains, such as antimicrobial compounds.

A novel approach to the discovery of next generation antimicrobial agents has centered on the development on the incorporation of singlet oxygen generating photoactive rigid photosensitizer molecules or macromolecules whose antimicrobial activity can be activated when exposed to ultraviolet and visible light. Unfortunately, these molecules have known cytotoxicity to mammalian cells and their broader use in clinical applications is precluded.

Thus, there is a critical need to design and synthesize new potent antimicrobials that have a broad biocidal spectrum and several modes of action mechanisms to prevent the microbes from becoming resistant over time.

Before proceeding to a description of the present invention, however, it should be noted and remembered that the description of the invention which follows, together with the accompanying drawings, should not be construed as limiting the invention to the examples (or embodiments) shown and described. This is so because those skilled in the art to which the invention pertains will be able to devise other forms of this invention within the ambit of the appended claims.

SUMMARY OF THE INVENTION

Disclosed herein are Eumelanin-inspired antimicrobial (e.g., antibacterial and antifungal) agents. The agents are potent antimicrobials that have a broad biocidal spectrum and are useful for killing microbes of many types, including those that are resistant to other conventional antibacterial and antifungal agents. In some aspects, the microbes are bacteria. In some aspects, the bacteria are resistant to killing or damage or the slowing of growth by at least one conventional antibacterial agent. In other aspects, the microbes are fungi. In some aspects, the fungi are resistant to killing or damage or the slowing of growth by at least one conventional antifungal agent. The agents thus are used in place of one or more conventional antimicrobials and/or in conjunction with, e.g., together with, one or more conventional antimicrobial agents.

As an example, herein is disclosed one embodiment of a Eumelanin-inspired antimicrobial capable of overcoming methicillin resistant *Staphylococcus aureus* (MSRA). By ligating quaternary ammonium functionalized "arms" on to a Eumelanin-inspired indole, with intrinsic antimicrobial activity, a cell wall destroying antimicrobial agent was derived from vanillin. This resulting antimicrobial, EIPE-1, had a minimum inhibitory concentration (MIC) of 16 µg/mL (17.1 µM) against a clinical isolate of MRSA obtained from an adult Cystic Fibrosis (CF) patient. The biocidal activity occurred within 30 minutes of exposure and resulted in cell membrane damage as visualized with SEM. Taken together, these studies demonstrate that EIPE-1 is effective at killing methicillin resistant *S. aureus*. In addition, cytotoxicity against eukaryotic cells (HeLa cells) seen for EIPE-1 required 4-5-fold greater concentrations and prolonged exposure (24 h) compared to the MIC against *S. aureus*. Thus, EIPE-1 is safe to use with respect to non-microbial, e.g., eukaryotic cells. This is highly significant as methicillin resistance is a huge problem in hospitals and patient treatment worldwide.

As a further example of an embodiment, EIPE-1 was tested against the fungal pathogens *Cryptococcus neoformans* and *Candida albicans*, which are responsible for over 200,000 yearly deaths. EIPE-1 has considerable antifungal effects on *C. neoformans* with a MIC of 1.749 µg/mL and a MIC of 2.705 µg/mL for *C. albicans*. In addition, scanning electron microscopy (SEM) and transmission electron microscopy (TEM) were used to test the efficacy of EIPE-1 on the exposed cells at varying time points. Cells exposed for four or more hours displayed structural changes to their cell wall. Overall, EIPE-1 does display potent anti-fungal activity against *C. neoformans* and *C. albicans*.

The Eumelanin-inspired indole core, methyl 4,7-dibromo-5,6-dimethoxy-1-methyl-1H-indole-2-carboxylate (DBI) (Scheme 1 below), has exhibited antimicrobial activity. For antimicrobial development, the indole core can serve as an excellent building block since it has multiple positions for the incorporation of bactericidal moieties. Applying synthetic approaches for the derivatization, the Eumelanin-inspired core was derivatized at the 4- and 7-positions with quaternary ammonium functionalized "arms" in order to prepare a novel antimicrobial agent. Herein, two examples are discussed: the antimicrobial activity of Eumelanin-inspired indole core (DBI) and the synthesis and enhanced antimicrobial activities of Eumelanin-inspired indoylenephenyleneethynylene, EIPE-1 (Scheme 1).

The foregoing has outlined in broad terms some of the more important features of the invention disclosed herein so that the detailed description that follows may be more clearly understood, and so that the contribution of the instant inventors to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the invention.

It is an object of the invention to provide a melanin-based antimicrobial of Formula I:

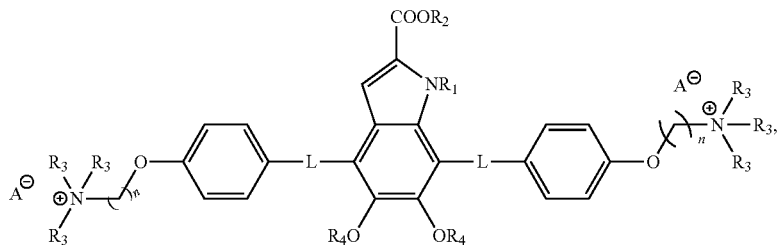

Formula I wherein
R1, R2, R3, and R4 are independently the same or different and are alkyl, alkenyl, alkynyl, cycloalkyl, aryl, perfluoroalkyl, a heterocyclic amine or a quaternary ammonium salt;
L is a linker comprising 1-6 carbon atoms;
A is a halogen, a carboxylic acid anion or an inorganic anion; and
n=1-10.
In some aspects, L is

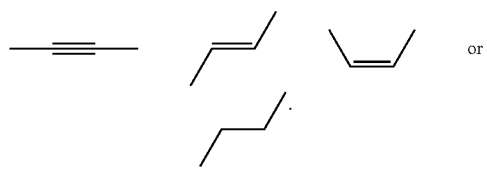

In further aspects, the melanin-based antimicrobial has a formula:

In additional aspects, the melanin-based antimicrobial is present in a composition comprising at least one carrier. In some aspects, the composition is a pharmaceutical composition, and the carrier is a pharmaceutically acceptable carrier. In further aspects, the pharmaceutical composition is formulated for intravenous, oral or topical administration.

In other aspects, the composition is formulated as a spray, foam or wash for disinfecting surfaces, containers and equipment.

Also provided as methods of treating or preventing a microbial infection in a subject in need thereof, comprising administering to the subject a therapeutically effective amount of a compound of Formula I. In some aspects, the microbial infection is caused by a bacteria. In additional aspects, the bacteria is a drug-resistant bacteria. In other aspects, the bacteria is a Gram positive bacteria and the compound is

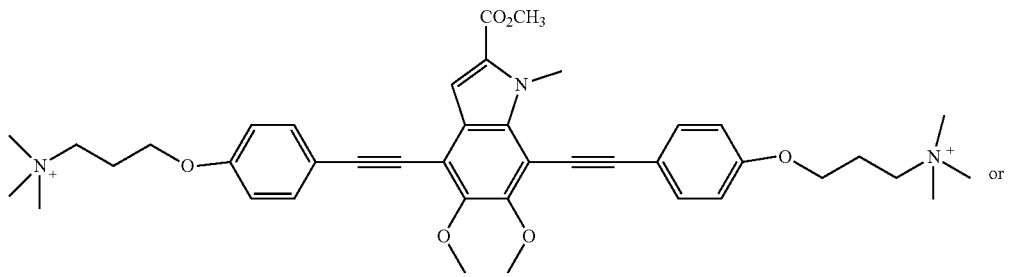

or

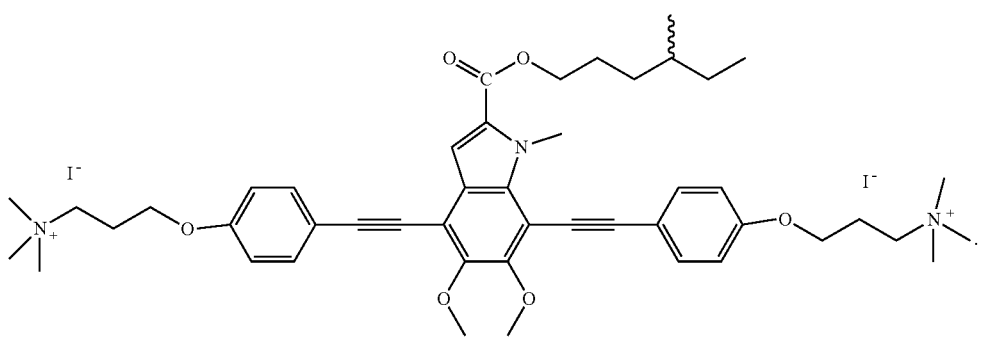

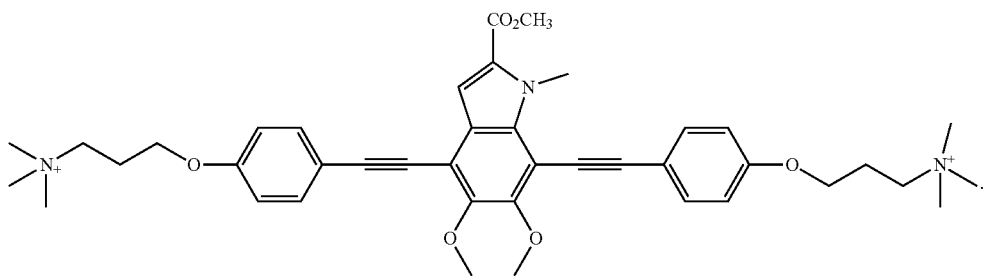

In further aspects, the Gram positive bacteria is *Bacillus subtilis, Staphylococcus aureus, Staphylococcus epidermidis* or *Enterococcus faecalis*. In some aspects, the *Staphylococcus aureus* is methicillin resistant *S. aureus* (MRSA).

In other aspects, the microbial infection is caused by a fungus. In some aspects, the fungus is a drug-resistant fungus. In further aspects, the fungus is *Candida albicans* or *Cryptococcus neoformans*. In additional aspects, the compound is

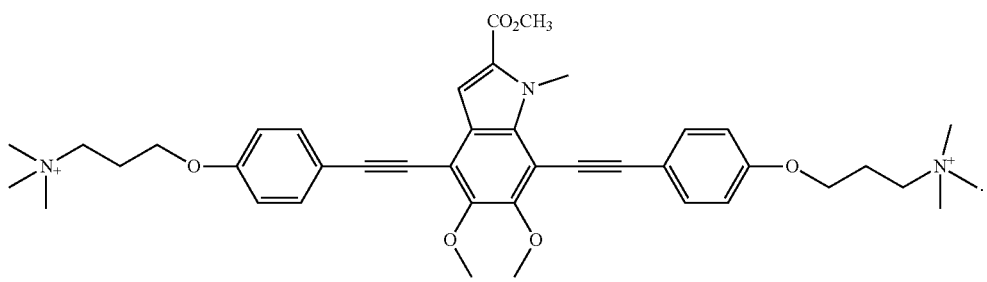

In some aspects, the subject is immunocompromised or immunosuppressed.

The invention also provides a method of killing or damaging a microbe, comprising contacting the microbe with at least one compound of claim 1.

BRIEF DESCRIPTION OF THE DRAWINGS

These and further aspects of the invention are described in detail in the following examples and accompanying drawings.

FIG. 1A-C illustrates antimicrobial effects of DBI on MRSA for an embodiment. (A) Resulting bacterial growth of MRSA measured by turbidity in cuvettes. (B) Recoverable growth on MRSA when exposed to DMSO (top) or DBI (bottom). (C) Recoverable MRSA (CFU/mL) after exposure to DMSO or DBI. Error bars represent standard deviation.

FIGS. 2A and B contains a Kirby-Bauer disc assay and cytotoxicity of DBI and EIPE-1 for an embodiment. (A) MRSA was inoculated as a bacterial lawn and 10 µL of EIPE-1 added to discs a-f as follows: (a) 1.0 mg/mL (b), 0.1 mg/mL (c) 0.01 mg/mL (d) 0.001 mg/mL, (e) 0.0001 mg/mL and (f) DMSO control. Zone sizes of (a) 2 mm, (b) 1.5 mm and (c) 1 mm observed after 24-hour incubation at 37° C. (B) The cytotoxicity of DBI and EIPE-1 were evaluated against the HeLa cell line up to concentrations of 250 µg/mL (610 µM) by measuring LDH release. DMSO was used as a negative solvent control. Error bars represent standard deviations.

FIG. 6 contains an example optical density for EIPE-1 and Amphotericin B drug inhibition of *C. neoformans* and *C. albicans* for an exemplary embodiment.

FIG. 7 contains exemplary scanning electron microscopy (SEMs) images of *C. neoformans* as a function of time for the control (left column) and EPIPE-1 treated (right column).

FIG. 8 contains mean MIC values for EIPE-1 using isolates ranged between 4 µg/mL and 11 µg/mL for *Candida* clinical samples.

DETAILED DESCRIPTION

Figure 3A:
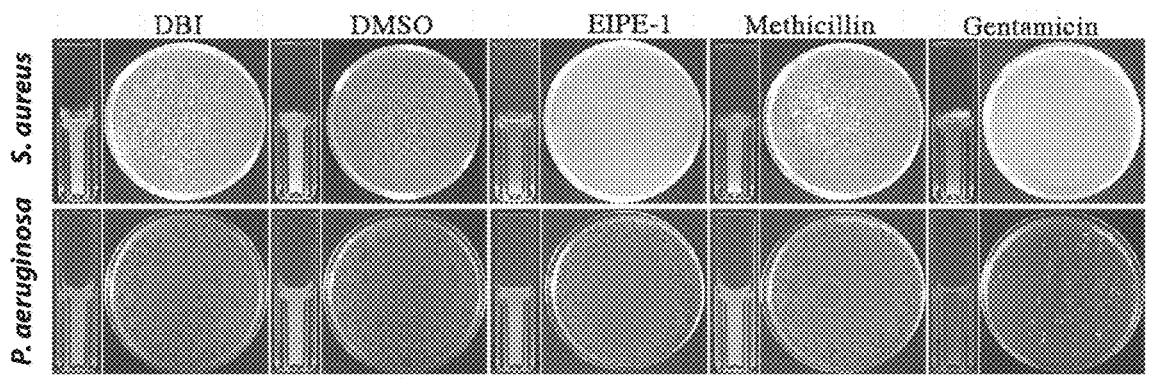
FIG. 3A-C shows the effects of EIPE-1 and selected conventional antibiotics on MRSA and PA. (A) Shown are broth and plate cultures of MRSA (top) and PA (bottom) exposed to DBI, DMSO, EIPE-1, Methicillin and Gentamicin. Recoverable CFU/mL corresponding to each condition for (B) MRSA and (C) PA. Error bars represent standard deviation. One-way ANOVA, *$p \leq 0.05$.

New melanin-inspired antimicrobial agents are described herein. The agents were developed by incorporating functional groups into a base structure shown below as Formula I.

Formula I

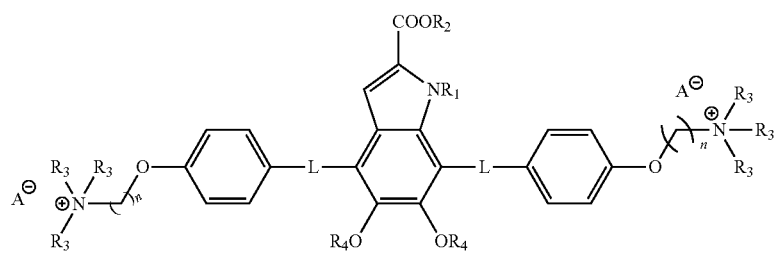

where R1-R4 are variable groups; L represents a linker; A represents halogen, a carboxylic acid anion or an inorganic anion; and n=1-10.

In some aspects, R1, R2, R3 and R4 are, independently, the same or different and are alkyl, alkenyl, alkynyl, cycloalkyl, aryl, perfluoroalkyl, a heterocyclic amine or a quaternary ammonium salt. In some aspects, the aryl group is an aromatic amine.

By alkyl a saturated straight chain or branched chain carbon group with 1 to 20 carbon atoms will be intended which may be substituted or unsubstituted. Examples include but are not limited to: methyl, ethyl, n-propyl, i-propyl, n-butyl, t-butyl, pentyl, hexyl, heptyl, octyl, nonyl and decyl.

The alkenyl group represents a straight chain or branched chain alkenyl group with 2 to 20 carbon atoms and comprising at least one double bond (C=C), i.e., is unsaturated. Examples include but are not limited to: vinyl, allyl, butenyl, pentenyl, geranyl, and farnesyl. An alkenyl may be substituted or unsubstituted.

The alkynyl group represents a straight chain or branched chain alkynyl group with 2 to 20 carbon atoms and at least one triple bond between 2 carbons, i.e., is unsaturated. Its examples include ethynyl, propynyl, and butynyl. An alkynyl may be substituted or unsubstituted.

The cycloalkyl group represents a saturated or unsaturated cycloalkyl group with 3 to 8 carbon atoms, and includes, for example, cyclopropyl, cyclobutyl, cyclopentyl, cyclohexyl, cycloheptyl, and cyclooctyl. Another example is a heterocyclic group in which one or more arbitrary methylene groups on the ring of the cycloalkyl group have been substituted by an oxygen atom, a sulfur atom, or an alkyl-substituted nitrogen atom.

The aryl group refers to a monovalent substituent formed by removing one hydrogen atom from an aromatic heterocyclic group or an aromatic hydrocarbon group. In some aspects, it represents a monovalent substituent formed by removing one hydrogen atom from an aromatic hydrocarbon group, such as, for example, phenyl, tolyl, xylyl, biphenyl, naphthyl, anthryl, and phenanthryl. The carbon atom on the ring of the aryl group may be substituted by one or more of a halogen atom, a lower alkyl group, a hydroxyl group, an alkoxyl group, or an aryloxy group, an amino group, a nitro group, and a trifluoromethyl group. In some aspects, the aryl group is an aromatic amine, examples of which include but are not limited to: aniline, fluoroaniline, chloroaniline, bromoaniline, nitroaniline, aminotoluene, fluoroaminotoluene, chloroaminotoluene, bromoaminotoluene, nitroaminotoluene, diaminobenzene, fluorodiaminobenzene, chlorodiaminobenzene, bromodiaminobenzene, nitrodiaminobenzene, diaminotoluene, 3,5-diethyltoluene-2,4-diamine, 3,5-diethyltoluene-2,6-diamine, dimethylthiotoluenediamine, benzidine, (di)fluorobenzidine, (di)chlorobenzidine, (di)bromobenzidien, (di)nitrobenzidine, (di)methylbenzidine, (di)ethylbenzidine, diaminodiphenylmethane, (di)fluorodiaminodiphenylmethane, (di)chlorodiaminodiphenylmethane, (di)bromodiaminodiphenylmethane, (di)methyldiaminodiphenylmethane, (di)ethyldiaminodiphenylmethane, diaminobenzophenone, (di)fluorodiaminobenzophenone, (di)chlorodiaminobenzophenone, (di)bromodiaminobenzophenone, (di)methyldiaminobenzophenone, (di)ethyldiaminobenzophenone, aminoimidazole, aminopyridine, bipyridinamine, etc.

The aryl group may be an aralkyl group i.e. an alkyl group bonded to an aryl group which is optionally substituted, e.g., one or more hydrogen atoms of the aryl group and the alkyl group may be substituted by substituents such as acyl, amino, aryl, alkyl, cycloalkyl, alkoxy, hydroxyl, nitro, or halogen. Examples of the aralkyl group are trityl, benzyl, phenethyl, tritylmethyl, diphenylmethyl, naphthylmethyl, and 4,4'-dimethoxytrityl (DMTr).

As used herein, a heterocyclic amine (HCA) refers to a chemical compound containing at least one heterocyclic ring, which, by definition, has atoms of at least two different elements, as well as at least one amine (nitrogen-containing) group. HCAs may be saturated or unsaturated and substituted or unsubstituted. Exemplary heterocyclic amines include but are not limited to: piperidines, piperazines, thiomorpholines, morpholines, pyrrolidines, etc.

When chemical groups of the disclosure are referred to as "substituted" or "optionally substituted", the substituents used for the substitution may include but are not limited to: amino, alkoxy, halogen, acyl, etc. If an amino group is present, it may or may not be substituted, but the amino group when substituted includes, for example, alkylamino, arylamino, and acylamino. Examples of the alkoxy group are methoxy, ethoxy, n-propoxy, 1-propoxy, n-butoxy, 1-butoxy, s-butoxy, t-butoxy, pentyloxy, hexyloxy, and phenoxy. Examples of the halogen atom are fluorine, chlorine, bromine, and iodine. As the acyl group, acetyl, formyl, propionyl, benzoyl, and benzyloxycarbonyl can be exemplified.

A perfluorinated compound (PFC) is an organofluorine compound containing only carbon-fluorines and C—C bonds but also other heteroatoms that are functional groups. PFCs have properties that result from the presence of fluorocarbons (containing only C—F and C—C bonds) and the functional group. "Perfluoroalkyl" refers to PFC comprising e.g., 1-10 carbon atoms and at least one perfluoroalkyl moiety, i.e., at least two F atoms present as —$C_nF_{2n}$—. Examples of functional groups include OH, $CO_2H$, chlorine, O, and $SO_3H$ and such groups may represent the point of attachment of a perfluoroalkyl group to an agent as described herein.

In some aspects, L is a linker comprising 1-6 carbon atoms (1, 2, 3, 4, 5, or 6 carbon atoms). The carbon atoms may be joined by one or more single bonds, and/or by one or more double bonds and/or one or more triple bonds, or by mixtures or these types of bonds, e.g., two single bonds and one double or triple bond, etc. If double bonds are present, they may be cis or trans. In some aspects, L is one of:

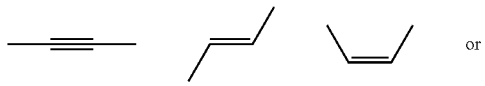 or 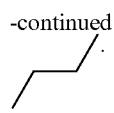

With respect to substituent A, the halogen may be e.g., Cl, Br, I or F; the carboxylic acid anion may refer to, for example, gluconate, glutamate, glycolate, carbonate, bicarbonate, or lactate; and the inorganic anion may be, for example, $SO_4^{2-}$, $NO_3^{-}$, and $H_2PO_4^{-}$, etc.

In some aspects, the melanin-inspired antimicrobial agent is

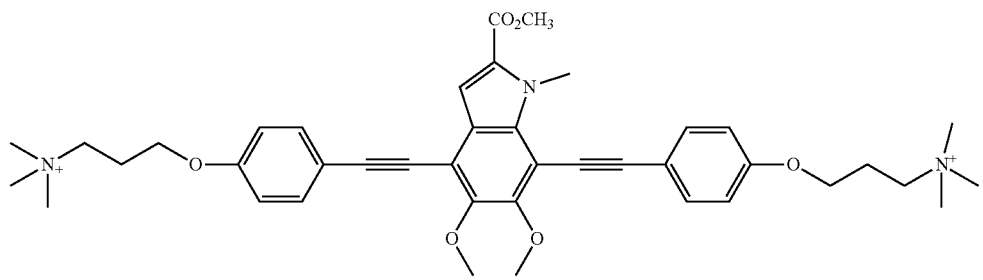

referred to herein as "EIPE-1" (indoylenephenyleneethynylene; IUPAC (3,3'-((((5,6-dimethoxy-2-(methoxycarbonyl)-1-methyl-1H-indole-4,7-diyl)bis(ethyne-2,1-diyl))bis (4,1-phenylene))bis(oxy))bis(N,N,N-trimethylpropan-1-aminium) iodide).

Figure 5:
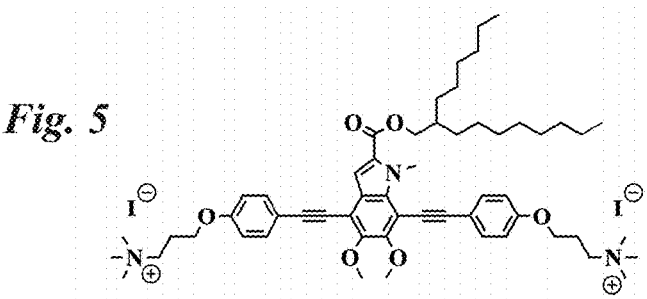
FIG. 5 depicts an exemplary embodiment, EIPE-PF, of the new proposed antimicrobials for biocidal activity against broad spectrum of microbes including Gram negative bacteria and fungi.

In a further aspect, modifications were made to the melanin-inspired core to enhance membrane permeability for Gram negative bacteria and kill them. The resulting compound, EIPE-2HD, is shown below and in FIG. 5. The synthesis is shown in Scheme 2 of Example 5.

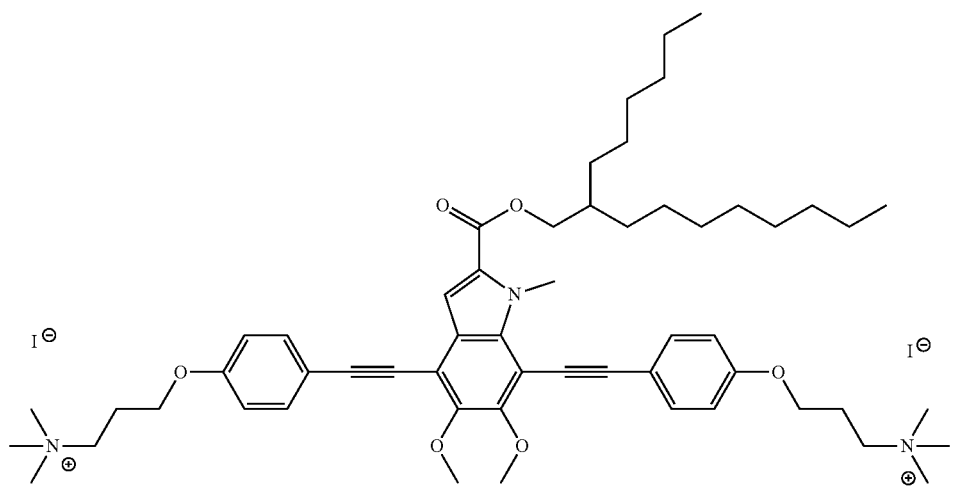

EIPE-HD

Pharmaceutical Compositions

In some aspect, the compounds described herein are delivered (administered) as a pharmaceutical composition to a subject or patient in need thereof. Generally, a "dose" or "dosage form" or "unit dosage form" of a pharmaceutical composition is administered. By "dose" is meant the amount of a compound administered to the human subject. The terms "dose", "dosage form" and "unit dosage form" as used herein, refers to physically discrete units suitable as unitary dosages, such as a pill, tablet, caplet, hard capsule or soft capsule, each unit containing a predetermined quantity of a drug. The preferred dosage of drug to be administered is likely to depend on such variables as the type and extent of the disorder, the overall health status of the particular subject, age, gender, species, the specific compound being administered, the excipients used to formulate the compound, and its route of administration. These parameters are best determined by one of skill in the relevant art such as a physician. However, in general, a "dose" will range from about 0.1 to about 1000 mg/kg of body weight of the recipient, e.g., about 0.5 to about 750 mg/kg; or about 1.0 to 500 mg/kg, or about 5.0 to 250 mg/kg or about 10.0 to 100.0 mg/kg. For example, the dosage may be about 1, 5, 10, 20, 30, 40, 50, 60, 70, 80, 90, 100, 125, 150, 175, 200, 225, 250, 275, 300, 325, 350, 375, 400, 425, 450, 475 or 500 mg/kg of body weight. The frequency of dosing can be, for example, about 1-4 times per day, weekly, monthly or as needed for the subject to prevent and/or treat the infection. Dosing may also be continuous, e.g., if administered by IV.

Such pharmaceutical compositions generally comprise at least one of the disclosed compounds, i.e., one or more than one (a plurality) of different compounds (e.g., 2 or more such as 2, 3, 4, 5, 6, 7, 8, 9, 10 or more) may be included in a single formulation. Accordingly, the present invention encompasses such formulations/compositions. The compositions generally include one or more substantially purified compounds as described herein, and a pharmacologically suitable (physiologically compatible) carrier, which may be aqueous or oil-based. In some aspects, such compositions are prepared as liquid solutions or suspensions, or as solid forms such as tablets, pills, powders, ointments, creams, and the like. Solid forms suitable for solution in, or suspension in, liquids prior to administration are also contemplated (e.g., lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g., pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as Tween® 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-O-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The compositions comprising at least one antimicrobial agent as described herein may be administered in vivo by any suitable route including but not limited to: inoculation or injection (e.g., intravenous, intraperitoneal, intramuscular, intraoral, intradermal, intraarterial, subcutaneous, intra-aural, intraarticular, intramammary, and the like); by topical application (e.g., on areas such as eyes, skin, nails, in ears, etc.); and/or by absorption through epithelial or mucocutaneous linings (e.g., nasal, oral, vaginal, rectal, gastrointestinal mucosa, and the like). Other suitable means include but are not limited to: inhalation (e.g., as a mist or spray); orally (e.g., as a pill, capsule, liquid, etc.); by ingestion of a food or food product containing the antimicrobial; as eye drops, incorporated into dressings or bandages (e.g., lyophilized forms may be included directly in the dressing), etc. In preferred embodiments, the mode of administration is topical or oral or by injection.

In addition, the compositions may be administered in conjunction with other treatment modalities such as substances that boost the immune system, various chemotherapeutic agents, other antibiotic agents, various pre- and/or pro-biotics (to help restore or maintain a healthy microbiome), and the like.

The pharmaceutical compositions of the invention are administered to subjects in therapeutically effective amounts. By "effective" amount is meant the amount of drug required to treat or prevent a fungal infection or a disease associated with a fungal infection, or at least to lessen the chances of the subject contracting an infection, or at least to lessen the severity and/or duration of an infection. The effective amount of drug used to practice the methods described herein for therapeutic or prophylactic treatment of conditions caused by or contributed to by a fungal infection varies depending upon the manner of administration, the age, body weight, and general health of the subject. Ultimately, the attending physician will decide the appropriate amount and dosage regimen. Such amount is referred to as an "effective" amount.

In some cases, the administration will completely "cure" the subject to whom the compound is administered, i.e., the infection is completely eradicated. However, those of skill in the art will recognize that much benefit can accrue to a patient if at least one symptom of an infection is lessened, e.g., to a point at which the subject's immune system can take over, or to a point at which another therapeutic measure can be used to treat the subject, etc.

In some instances, the subject is at risk for developing a bacterial or fungal infection or a related condition and receives one or more doses before developing symptoms or signs of an infection. In some instances, the subject has already developed an infection or a related condition and receives one or more doses. The timing of the administration of the dose(s) of compound 1 may be optimized by a physician to reduce the risk of or to treat a bacterial and/or fungal infection in a human subject.

Subjects in whom microbial infections are treated are generally mammals and may be humans. However, the practice of the invention is not limited to mammals and humans. Veterinary uses of the compounds to prevent and treat infections are also encompassed, including for non-mammalian species. More generally, an infection can be any situation in which the presence of a microbial population(s) is damaging to a host body.

In some aspects, the subjects that are treated are "immunocompromised" or "immunosuppressed". As used herein, the term "immunocompromised" or "immunosuppressed" refers to a subject (e.g., a human) who has immune system that functions in an abnormal or incomplete manner, for example, wherein the subject does not have the ability to respond normally to an infection due to what is referred to herein as an "impaired immune system", "weakened immune system", or "reduced immune system". The subject's immune system can be weakened or compromised by a disease (e.g., an HIV infection, an autoimmune disease, cancer), a medical procedure (e.g., an organ transplant (e.g., a solid organ transplant) or a bone marrow transplant), a medical treatment (e.g., an immunosuppressant), and/or a pathogen (e.g., bacteria, fungus, virus). The immune system of the host may also have a congenital defect that renders the host more susceptible to infection. Immunocompromised subjects may be found more frequently among infants, the elderly, and individuals undergoing extensive drug or radiation therapy. Accordingly, aspects of the invention involve the treatment of pediatric and geriatric patients, or patients at risk of a nosocomial infection. Particular patient populations may for example include patients with compromised immune systems due to HIV infection or AIDS, cancer, solid organ transplantation, stem cell transplantation, sickle cell disease or asplenia, congenital immune deficiencies, or chronic inflammatory conditions.

In some aspects, compositions comprising one or more of the compounds disclosed herein are intended for external use on a subject, e.g., washes, creams, ointments, etc. This aspect is especially pertinent to the treatment of the hands of, e.g., medical practitioners (doctors, nurses, etc.) even if they are not suspected of having an active infection that will be detrimental to them. Such measures can be used, e.g., to prevent nosocomial infections caused by medical personnel unknowingly passing e.g., drug-resistant microbes to patients.

Cleaning/Disinfecting Compositions

In other aspects, the compounds disclosed herein are used for the sanitization of, e.g., in animate surfaces and/or medical equipment. As such, the compounds are used to treat, e.g., medical equipment to eradicate or prevent the growth of microbes thereon. This procedure prevents the transmission of infectious organisms from the equipment to a subject. For example, this use of the compounds serves to prevent nosocomial infections. Medical equipment that can be treated includes, but are not limited to: tubing, catheters, IV lines, surgical instruments, etc. In this aspect, the equipment is washed, rinsed, soaked, sprayed, or otherwise contacted directly with an amount of the compound, e.g., a solution of the compound, for a period of time sufficient to kill bacteria and fungi that are present on or in the equipment. In further aspects, surfaces may also be cleansed/disinfected using an amount of the compound, e.g., a solution of the compound, and for a period of time sufficient to kill bacterial and fungi that are present thereon. These methods can be used, for example, in medical settings, in food preparation settings, nursing homes, etc. Thus, the invention also provides methods of killing or damaging and/or slowing the growth of microbes. The methods include contacting the microbes with a quantity of an antimicrobial compound disclosed herein that is sufficient to kill, damage and/or slow the growth of the microbe.

Such compositions include at least one compound (or more than one compound) as described herein at a concentration of from about, for example, 1 mM or less to about 10M or more, such as about 1, 10, 100, 500, or 750 mM, or about 1, 2, 3, 4, 5, 6, 7, 8, 9, or 10 M. Such compositions may include many of the same additional components as those listed above for pharmaceutical compositions, except that the components are not necessarily safe for ingestion or for external use on a living subject.

The compositions may be in the form of, for example, sprays, foams, liquids, etc. that are used to deodorize, clean, sanitize, and/or disinfect porous or hard surface articles and hard surfaces or containers. Such composition may be used alone or in combination with other disinfectants such as various alcohols, peroxide compounds, quaternary ammonium compounds, acids, amines, ammonia-based compounds, detergents, etc. either as separate compositions or together in the same composition. Examples of additional disinfecting compositions and their formulations and uses are described, for example, in published US patent applications 20210204543, 20200267973, 20200245616, 20200138021, 20190166828, the entire contents of each of which is hereby incorporated by reference in entirety.

Preventing and Treating Fungal Infections

In some aspects, the infection that is prevented or treated is a fungal infection. In some aspects, the infection that is caused by a fungus that is resistant to at least one other anti-fungal agent. As used herein, the term "antifungal agent" refers to a therapeutic compound or bioactive agent which may be used to treat a fungal infection in a patient. An antifungal drug is a medication used inhibit the growth of or destroy fungi. Antifungal agents include, for example, polyene antifungals, imidazole, triazole and thiazole antifungals, allylamines, echinocandins, griseofulvin, flycystosine, undecylenic acid, among others. In some embodiments, the fungi are resistant to one or more antifungal compounds including but not limited to clotrimazole, econazole, ketoconazole, itraconazole, fluconazole, posaconazole, voriconazole, miconazole, tioconazole, terbinafine, and amorolfine.

In some aspects, the fungal infection that is prevented or treated is not caused by a fungus that is resistant to another antifungal agent, i.e., the present compounds can also be used a front-line anti-fungal agents.

The fungal infection that is prevented or treated is caused by one or more fungi, for example, *Candida, Trichophyton, Aspergillus, Malassezia* or *Cryptococcus* fungus. Embodiments described herein as relating to *C. albicans* and/or *C. neoformans* should be understood to apply more broadly to embodiments encompassing polymorphic fungi, dimorphic fungi, and/or pathogenic fungi in general. Examples of other fungi that can cause infections to be prevented and/or treated by the compounds include but are not limited to: *Candida auris, Cryptococcus neoformans, Crypotococcus laurentii, Cryptococcus albidus, Cryptococcus gattii, Pneumocystis jirovecii, Stachybotry chartarum, Coccidioides immitis, Paracoccidioides brasiliensis, Ustilago maydis, Blastomyces dermatitides, Histoplasma capsulatum, Sporothrix schenckii,* and *Emmonsia sp.*

In some aspects, the anti-fungal agent is EIPE-1

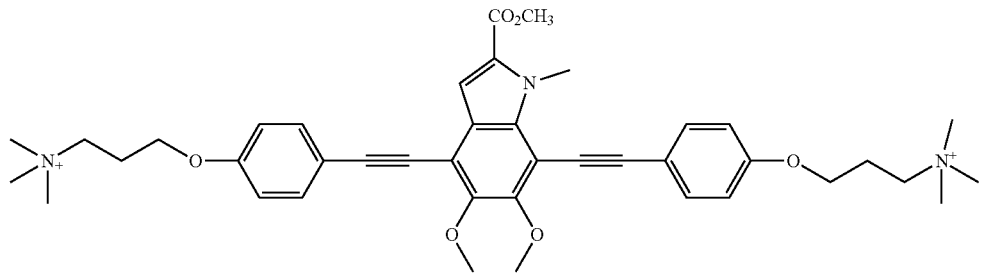

Other relevant information concerning pharmaceutical compositions and their preparation and administration to treat fungal infections is found, for example, in published US patent applications 20200316033, 20210002346, 20210179667 and 20200060273, the complete contents of each of which is hereby incorporated by reference.

Preventing and Treating Bacterial Infections

In some aspects, the infection that is prevented or treated is a bacterial infection. In some aspects, the infection that is caused by a bacteria that is resistant to at least one other anti-bacterial agent. As used herein, the term "antibacterial agent" refers to a therapeutic compound or bioactive agent which may be used to treat a bacterial infection in a patient. An antibacterial drug is a medication used inhibit the growth of or destroy bacteria. Antibacterial agents include, for example, methicillin, kanamycin, streptomycin, amikacin, gentamicin, isepamicin, netilmicin, sisomicin, tobramycin, vancomycin, various aminoglycosides, etc. The infection that is treated may be caused by bacteria that is resistant to at least one of these anti-bacterial agents. Common drug resistant bacteria include but are not limited to: methicillin-resistant *Staphylococcus aureus* (MRSA), vancomycin-resistant *Enterococcus* (VRE), multi-drug-resistant *Mycobacterium tuberculosis* (MDR-TB), carbapenem-resistant Enterobacteriaceae (CRE) gut bacteria, etc.

In some aspects, the bacterial infection that is prevented or treated is not caused by a bacteria that is resistant to another antibacterial agent, i.e. the present compounds can also be used a front-line antibacterial agents against bacterial infection.

As noted elsewhere herein, the agent EIPE-1

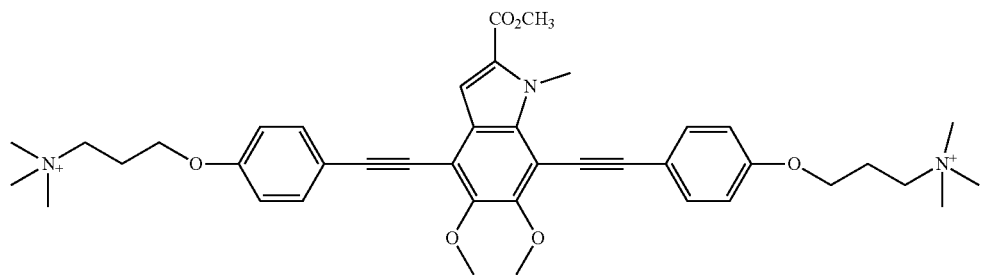

is especially useful to treat infections causes by Gram positive bacteria (e.g., *Bacillus subtilis* ATCC 6633, *Staphylococcus aureus* ATCC 25923, *Staphylococcus aureus* T-5706, *Staphylococcus aureus* ATCC 29213, *Staphylococcus aureus* SFL 8, *Staphylococcus aureus* SFL 64, *Staphylococcus epidermidis*) whereas the agent EIPE-2HD

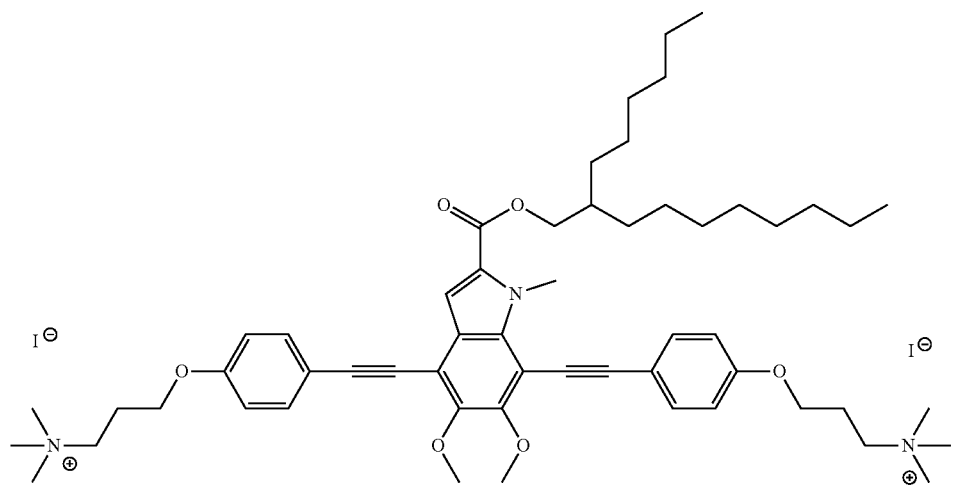

can be effective against Gram negative bacteria.

In some aspects, the bacteria that cause the infection are present in or as a biofilm.

Examples of bacteria that cause infections that may be prevented or treated using the compounds disclosed herein include but are not limited to: Closiridioides spp. (e.g., Clostridioides dificile and Clostridioides *mangenotii*), *Clostridium clostridioforme, Clostridium perfringens, Eubacterium lentum, Peptostreptococcus* spp., *Serratia marcescens, Streptococcus anginosus, Staphylococcus aureus* (methicillin susceptible and resistant isolates), *Staphylococcus epidermidis* (methicillin susceptible and resistant isolates), *Stenotrophomonas maltophilia, Streptococcus agalactiae, Streptococcus constellaus, Streptococcus pneumoniae* (penicillin susceptible and resistant isolates), *Streptococcus pyogenes*, or *Streptococcus pyogenes*, among others.

Other Applications of the Technology

General methods for killing or damaging microbes by contacting them with at least one compound as disclosed herein, under conditions and for a period of time sufficient to kill or damage the microbes. For example, contact with the agent for at least about 30-60 seconds, or about 1-2 minutes, or about 5 minutes or longer (e.g., soaking for one hour or more), may result in breaching, puncturing or disrupting the cell wall of the microbe, leading to cell death, cessation of metabolism, the inability to reproduce, etc. These methods are useful both in vivo (e.g., in patients) and in vitro (e.g., to sterilize medical equipment and other surfaces, such as in food preparation facilities). Such methods are typically performed at ambient temperature, which may be, e.g., room temperature (about 25° C.) or cooler (e.g., at the temperature of an operating room: 66 to 68 degrees Fahrenheit).

In addition, the invention provides methods of making an antimicrobial agent. The methods comprise those which are illustrated in Scheme 1 of Example 1 and Scheme 2 of Example 5. Those of skill in the art will recognize that the particular reagents (e.g., solvents) and reaction conditions (e.g., temperatures) depicted in the Schemes may be altered or adapted somewhat and that the methods would still be successful in producing, e.g., EIPE-1 and EIPE-HD. In addition, other reactants as described herein under compositions may be used or substituted in the Schemes to add, e.g., alkyl chains of varying lengths, alkenyl groups instead of alkyl groups, etc. to arrive at other variants of Formula I.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not to be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

For purposes of the instant disclosure, the term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e.g., "about", "substantially", "approximately", etc.) should be interpreted according to their ordinary and customary meanings as used in the associated art unless indicated otherwise. Absent a specific definition and absent ordinary and customary usage in the associated art, such terms should be interpreted to be ±10% of the base value.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Further, it should be noted that terms of approximation (e.g., "about", "substantially", "approximately", etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

Still further, additional aspects of the instant invention may be found in one or more appendices attached hereto and/or filed herewith, the disclosures of which are incorporated herein by reference as if fully set out at this point.

While this invention is susceptible of embodiment in many different forms, there is shown in the drawings, and will herein be described hereinafter in detail, some specific embodiments of the instant invention. It should be understood, however, that the present disclosure is to be considered an exemplification of the principles of the invention and is not intended to limit the invention to the specific embodiments or algorithms so described.

EXAMPLES

Biomacromolecular pigments, melanins, which give rise to all coloration of hair, skin, and eyes in humans and animals, can act as a natural sunscreen to protect against harmful UV light. The black-brown variety of melanin, Eumelanin, is known to be composed 5,6-dihydroxyindole and 5,6-dihydroxyindole 2-carboxylic acid. Biocompatible, biodegradable and peculiar physicochemical properties of Eumelanin has marked it as a promising material in medicine and bioelectronics.

Among many functions and properties, Eumelanin also possesses an intrinsic antimicrobial activity. Eumelanin is produced by a number of microorganisms, including pathogenic bacteria and fungi, and has been shown to interfere with numerous host defense mechanisms. The ability of Eumelanin to protect microbes from host defenses is relevant to antimicrobial therapy because the clinical efficacies of some antimicrobial drugs are complemented by host immune defenses. Hence, modifying naturally occurring compounds can lead to more effective agents.

Example 1

Materials and Methods

Tetrakis(triphenylphosphine)palladium(0) [Pd(PPh$_3$)$_4$], copper (I) iodide (CuI) and 3-chloro-N,N-dimethylpropan-1-amine hydrogen chloride were purchased from Sigma-Aldrich. Iodomethane and 4-iodophenol were purchased from Alfa Aesar. Mannitol salts agar was purchased from Criterion Culture Media by Hardy Diagnostics. Luria-Bertani broth, Mueller Hinton agar, Lactate Dehydrogenase (LDH) Quantification Kit and Live/Dead BacLight bacterial viability kit were purchased from ThermoFisher. All other solvents and reagents were purchased from Fisher Scientific. All commercial reagents were used as received. Methyl 4,7-dibromo-5,6-dimethoxy-1-methyl-1H-indole-2-carboxylate (DBI) was synthesized according to a reported procedure. Et$_3$N was freshly distilled before use. Unless otherwise specified, all reactions were conducted in oven-dried glassware under a nitrogen atmosphere. Anhydrous tetrahydrofuran (THF) and chloroform (CHCl$_3$) were obtained from a solvent purification system under ultrapure argon. Reactions were monitored by thin layer chromatography on silica G TLC plates (Sorbent Technologies No. 1634126). Purifications were performed by column chromatography on silica gel (Sorbent Technologies, 40-63 m particle size) or neutral alumina (Sorbent Technologies, 32-63 m particle size). $^1$H- and $^{13}$C-NMR spectra were measured on a Bruker Avance 400 MHz instrument. High-resolution mass spectrometry was performed using an Orbitrap operated in the FT mode to provide a nominal resolution of 100000.

Synthesis of methyl 4,7-diethynyl-5,6-dimethoxy-1-methyl-1H-indole-2-carboxylate (1)

To a 25-mL Schlenk flask was added DBI (500 mg, 1.22 mmol) under argon atmosphere, and followed by the addition of Pd(PPh$_3$)$_4$, (71 mg, 5 mol %) and CuI (3 mg, 2.5 mol %). To the mixture was added Et$_3$N (10 mL), followed by trimethylsilylacetylene (603 mg, 6.14 mmol), and the reaction mixture was heated overnight at 80° C. The final mixture was cooled to room temperature, filtered through celite and concentrated under vacuum to give a yellow solid. To this solid was added THF (5 mL), MeOH (5 mL) and K$_2$CO$_3$ (696 mg, 6.1 mmol). The new reaction mixture was stirred at room temperature for 1 h, and then distilled water (10 mL) was added. The resulting mixture was allowed to stir for another 10 minutes. The mixture was extracted with ethyl acetate (3×15 mL), dried with MgSO$_4$, and concentrated under in vacuo. Column chromatography of the concentrate on silica gel using hexane/ethyl acetate (98:2) as eluent afforded a brown solid (218 mg, 60%), mp 137° C. (dec). $^1$H NMR (400 MHz, CDCl$_3$): δ 7.35 (s, 1H), 4.46 (s, 3H), 3.98 (d, J=2.1 Hz, 6H), 3.90 (s, 3H), 3.71 (s, 1H), 3.62 (s, 1H). $^{13}$C NMR (101 MHz, CDCl$_3$): δ 161.99, 155.74, 150.76, 134.45, 129.18, 124.78, 110.24, 110.20, 102.57, 88.09, 86.01, 61.72, 61.63, 51.75, 33.54. HRMS (ESI) [M]$^+$ Calcd for C$_{17}$H$_{16}$NO$_4$: m/z 298.1074; Found: 298.1062.

Synthesis of 3-(4-iodophenoxy)-N,N-dimethylpropan-1-amine (2)

Compound 2 was synthesized according to the previously reported procedure with an 83% yield. Briefly, the "arms" of the EIPE-1 were constructed by reacting p-bromophenol with 3-chloro-N,N-dimethylpropan-1-amine hydrochloride under basic conditions to afford compound 2 in 88% yield. The spectrum were consistent with the previously reported data.

Synthesis of 3,3'-((((5,6-dimethoxy-2-(methoxycarbonyl)-1-methyl-1H-indole-4,7-diyl)bis(ethyne-2,1-diyl))bis(4,1-phenylene))bis(oxy))bis(N,N,N-trimethylpropan-1-aminium) iodide (EIPE-1)

Into a microwave reactor vial was added methyl 4,7-diethynyl-5,6-dimethoxy-1-methyl-1H-indole-2-carboxylate (1) (50 mg, 0.168 mmol) and 3-(4-iodophenoxy)-N,N-dimethylpropan-1-amine (2) (107 mg, 0.353 mmol). Then Pd(PPh$_3$)$_4$ (9.7 mg, 5 mol %) and CuI (0.8 mg, 2.5 mol %) were added under argon atmosphere, and the system was sealed. To this mixture was added freshly distilled Et$_3$N (1 mL) and the reaction mixture was stirred for 24 h at 85° C. The final solution was cooled to room temperature, filtered through celite and neutral alumina, and then concentrated in vacuo to give a yellowish orange solid. The solid was then dissolved in dry CHCl$_3$ (1 mL), and iodomethane (0.1 mL, 1.61 mmol) was added. The reaction mixture was then stirred overnight at room temperature. A red solid precipitated which was filtered and washed with CHCl$_3$ and dried in air to afford EIPE-1 (57 mg, 36%), mp 234° C. (dec). $^1$H NMR (400 MHz, DMSO-d$_6$): δ 7.64-7.50 (m, 4H), 7.31 (s, 1H), 7.06 (m, 4H), 4.47 (s, 3H), 4.13 (t, J=5.0 Hz, 4H), 3.96 (d, J=1.6 Hz, 6H), 3.87 (s, 3H), 3.51 (t, J=7.6 Hz, 4H), 3.12 (s, 18H), 2.22 (m, 4H). $^{13}$C NMR (101 MHz, DMSO-d$_6$): δ 161.62, 159.26, 154.51, 150.13, 133.85, 133.65, 133.08, 129.48, 123.89, 115.62, 115.56, 115.09, 114.99, 110.32, 109.71, 103.33, 100.38, 98.98, 82.71, 82.04, 65.46, 63.37, 61.97, 61.90, 52.81 (t, Jc-N=3.4 Hz), 52.42, 33.93, 22.98. HRMS (ESI) [M]$^{2+}$ Calcd for C$_{41}$H$_{51}$N$_3$O$_6$: m/z 340.6883; Found: 340.6866.

Bacterial Strains, Growth Conditions, and Media.

The methicillin resistant *Staphylococcus aureus* (MRSA) and *Pseudomonas aeruginosa* (PA) strains used in this study are clinical isolates obtained from an adult CF patient at the Cystic Fibrosis Clinic at the OU Children's Hospital (Oklahoma City, Okla.). *Escherichia coli* (*E. coli*) and *Enterococcus faecalis* (*E. faecalis*) were obtained from American Type Culture Collection (ATCC). The strains were grown overnight with shaking at 37° C. (220 RPM) in 15 mL of Luria-Bertani (LB) broth. The overnight culture was sub-cultured the next day before use for the MIC experiments. All sub-cultures consisted of 1 mL of the overnight culture, mixed with 10 mL of Mueller Hinton broth. The working stock of the EIPE-1 and DBI was prepared by dissolving 1 mg of each in 1 mL of DMSO.

Minimum Inhibitory Concentrations (MIC) Determination.

The minimum inhibitory concentrations (MICs) were determined by the broth microdilution method, following the guidelines of the Clinical and Laboratory Standards Institute (CLSI). Two-fold serial dilutions of EIPE-1, DBI, and Arm (starting with 1 mg/mL) were prepared in a 100 μL volume in 96-well microtiter plates. The dilution series included DMSO as a negative control. The bacterial culture (900 μL) was normalized to an OD$_{600}$ of 0.2 and was then added to each well. Plates were incubated with shaking at 220 RPM at 37° C., and the MIC was determined based on the lowest concentration at which no visible growth of the bacterial isolate was observed.

Susceptibility Testing by the Kirby-Bauer Disc Diffusion Methods.

The susceptibility of MRSA to EIPE-1 was determined by the Kirby-Bauer disc diffusion method. Using a cotton swab applicator, a lawn of the *S. aureus* clinical isolate was placed onto Mueller Hinton agar plates to cover the entire surface of the plate. Filter discs (size=6 mm) were added onto the bacterial lawn. EIPE-1, DBI, and DMSO (10 μL each) were then added onto the filter discs. The susceptibility was determined based on an evaluation of the size of the zones of clearance after 24 h of incubation at 37° C.

Live/Dead Staining of EIPE-1 Treated *S. aureus*.

MRSA was grown overnight in 10 mL of LB broth, sub-cultured (5 mL of overnight culture added to 20 mL LB) and grown for 3 h. Bacterial culture (150 μL) were removed and transferred to a 1.5 mL centrifuge tube, which was treated with DMSO, EIPE-1 (0.01 mg/mL) or DBI (0.01 mg/mL) for 30 minutes. Equal amounts of the two dyes (SYTO 9 dye, 3.34 mM in DMSO), and propidium iodide (20 mM in DMSO) were mixed. Then 0.5 μL of the dye mixture was added to each tube of treated MRSA cultures. Wet mounts were prepared on glass slides for imaging live and dead MRSA, and Differential Interference Contrast (DIC) images were obtained using a Leica DMI600B fluorescent microscope. To determine the percentage of bacteria alive and dead, the total bacteria in each condition were counted in 20 fields of view and graphed using Prism 5.0.

Scanning Electron Microscopy.

MRSA was grown overnight in 10 mL of LB broth, sub-cultured (5 mL of overnight culture added to 20 mL LB) and grown for 3 h. MRSA culture (300 µL) were removed, placed into a 1.5 mL tube, and treated with DMSO or EIPE-1 (0.01 mg/mL) for 30 minutes. Each sample was placed on glass coverslips (treated with poly-L-lysine) in a 24 well plate and fixed with 2% glutaraldehyde (in 0.1 M sodium cacodylate buffer) for 2 h at room temperature. After fixation, samples were washed three times with 0.1 M sodium cacodylate buffer. Samples were then fixed with 1% osmium tetroxide in water for 1 h at room temperature and were then washed three times with 0.1 M sodium cacodylate buffer. The samples were then dehydrated with an ethanol series (once with 50%, 70%, 90%, 95% and thrice with 100% ethanol). Samples were dried using hexamethyldisilazane (HAMDS) and then were mounted on stubs. Finally, samples were coated with gold and palladium using an automated sputter coater. Micrographs were acquired using Quanta 600 Scanning electron microscope.

Cytotoxicity

HeLa cells were cultured in 96-well plates at 37° C. and 5% $CO_2$ in Roswell Park Memorial Institute (RMPI) 1640 medium with 5% Fetal Bovine Serum (FBS). Once HeLa cells reached 95% confluency, the media was replaced with media containing various concentrations of EIPE-1, DBI or DMSO for 24 hours. Cell cytotoxicity was measured using the lactate dehydrogenase (LDH) leakage assay. Results were compared to maximum values of lysed cells in control wells and were graphed as percent relative cytotoxicity using Prism 5.0.

Colony Forming Units Quantitation.

To determine CFUs of PA and MRSA after exposure to DMSO, DBI, EIPE-1, Gentamicin or Methicillin, 10-fold serial dilutions were prepared in 96-well micro plates using multichannel pipettes. For each dilution, 25 ptL of each sample was pipetted onto a plate containing agar medium and incubated for 18 h at 37° C. The number of colonies for each dilution were counted and used to back calculate the number of bacteria per mL (CFU/mL) in each original bacterial culture.

Statistical Analysis.

All data was graphed using Prism 5.0. Two-tailed unpaired t test was used to analyze percentage of live/dead bacteria. One-way ANOVA with the Newman-Keuls Post-test was used to analyze the recoverable CFU/mL of bacteria.

Results and Discussion

Antimicrobial Activity of Eumelanin Inspired Core (DBI).

The Eumelanin-inspired indole core (DBI), as disclosed in issued U.S. patent Ser. No. 10/774,175, the complete contents of which is hereby incorporated by reference in entirety, was studied to determine if it retained the intrinsic antimicrobial activity possessed by native Eumelanin. DBI was tested against MRSA.

DBI was found to retain its intrinsic antimicrobial activity against MRSA (FIG. 1), as follows: A MRSA bacterial culture was grown overnight and sub-cultured (1 mL into 10 mL of Mueller Hinton Broth) to which either DMSO or DBI was added. After 4 h of growth, the resulting cultures were plated onto Mannitol Salts Agar (MSA). Decreased bacterial growth and decreased fermentation of the Mannitol (retention of the reddish hue of the MSA plate) could be seen in the MRSA culture exposed to DBI (FIG. 1A) which was confirmed with decreased recoverable CFUs (FIGS. 1B and 1C). Despite the reduced recoverable CFUs (average of $1.78 \times 10^8$ for DMSO control to average of $1.19 \times 10^7$ for DBI) seen when MRSA was exposed to DBI, a MIC could not be determined as all concentrations of DBI tested resulted in some growth indicating a retardation rather than inhibition of MRSA growth.

Synthesis of an Exemplary Antimicrobial Agent EIPE-1.

In order to enhance the intrinsic antimicrobial efficacy of DBI against pathogenic bacteria, two bactericidal moieties ligated onto the core molecule to generate the Eumelanin-inspired indoylenephenyleneethynylene (EIPE-1) (Scheme 1). The synthesis of EIPE-1 was conducted by Sonogashira coupling of DBI with trimethylsilylacetylene, followed by a deprotection to yield the diacetylene compound 1 in 65% yield. The "arms" of the EIPE-1 were constructed by reacting p-bromophenol with 3-chloro-N,N-dimethylpropan-1-amine hydrochloride under basic conditions to afford compound 2 in 88% yield. Compounds 1 and 2 were coupled under Sonogashira coupling conditions, followed by N-methylation with methyl iodide to afford EIPE-1 in 36% yield.

Scheme 1. Synthesis of Exemplary Eumelanin-Inspired Indoylenephenyleneethynylene (EIPE-1)

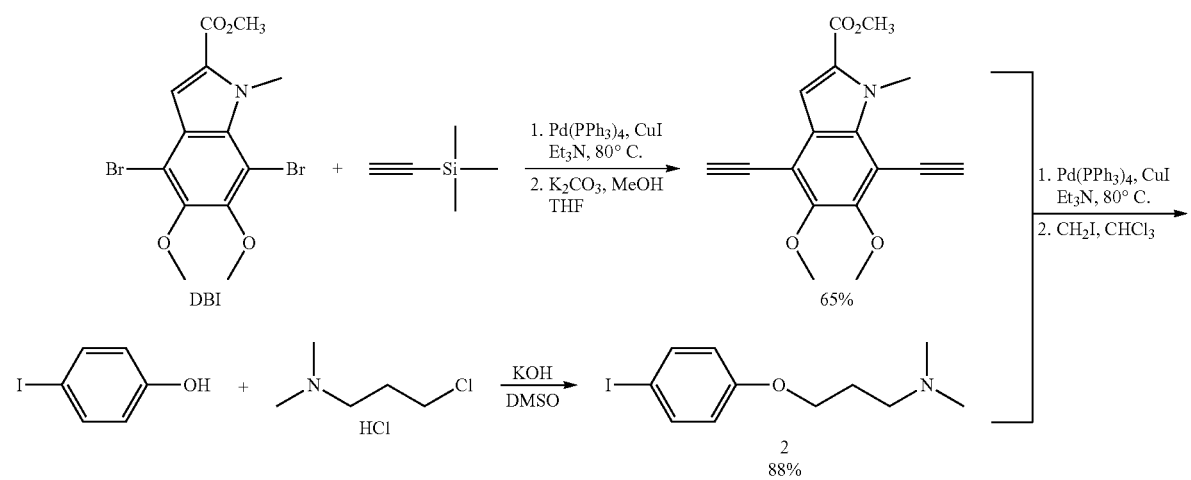

-continued

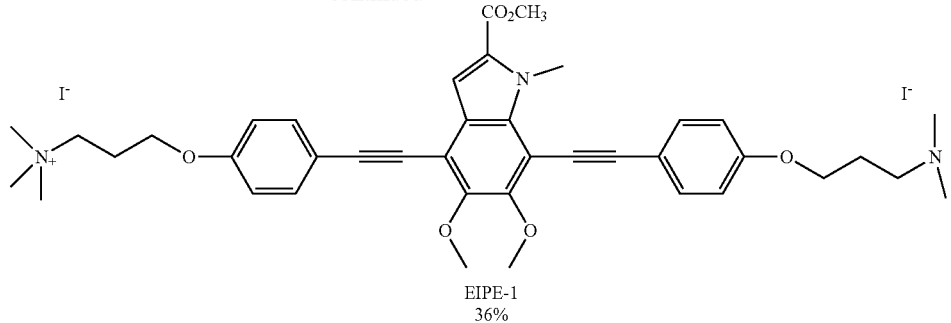

EIPE-1
36%

The EIPE-1 structure and purity were confirmed by NMR and HRMS analysis, along with a melting point determination. The incorporated bactericidal groups were expected to exhibit same antibiotic mechanism against bacterial cells as Triton B, Polymyxins and other cationic cell wall disrupting compounds. These systems target the stability of the bacterial outer membrane, resulting in lysis and ultimately leading to the death of the bacterial cell.

Antimicrobial Activity of EIPE-1.

The efficacy of compound EIPE-1 was tested by the Kirby-Bauer disc assay. The Kirby-Bauer disc assay assesses the sensitivity of bacteria to antimicrobial agents. If the bacteria are sensitive to the antimicrobial being tested, then a zone of inhibition of bacterial growth is seen around the filter disc containing the antimicrobial. The Kirby-Bauer disc assay was used to test the antimicrobial efficacy of EIPE-1 against MRSA. EIPE-1 was reconstituted at 1 mg/mL in DMSO and serially diluted ($10^{-1}$ to $10^{-5}$) after which 10 µL of each dilution (and DMSO as a solvent control) was added to a separate disc on an LB plate inoculated with a lawn of bacteria. The plates were incubated at 37° C. for 24 h, and the resulting radii zone sizes around each disc were then measured. The newly generated EIPE-1 compound was observed to inhibit MRSA growth as can be seen by zones of clearing around the discs displayed in FIG. 2A for concentrations of 1.0 mg/mL, 0.1 mg/mL and 0.01 mg/mL. The solvent negative control, DMSO, did not affect growth of MRSA (FIG. 2A, disc f). These experiments demonstrated that EIPE-1 has antimicrobial activity against MRSA (FIG. 2A). The functionalized "arms" of the EIPE-1 did not exhibit any antimicrobial activity independent of the DBI core confirming the fully assembled EIPE-1 was needed for antimicrobial activity.

Cytotoxicity Studies.

Host cell cytotoxicity against HeLa cells was examined for both DBI and EIPE-1 (FIG. 2B). LDH release was examined after 24-hour exposure to varying concentrations of DBI, DMSO and EIPE-1. DMSO was used as a solvent control and did not have any cytotoxic effects on HeLa cells. A maximal cytotoxicity of 50% was seen at concentrations above 62.5 µg/mL (66.8 µM) for EIPE-1 whereas 30% cytotoxicity was seen for the DBI at 250 µg/mL (610 µM). The cytotoxicity seen for EIPE-1 required 4-5-fold greater concentrations and prolonged exposure (24 h) than the MIC determined against S. aureus. Thus, EIPE-1 is relatively safe to use with respect to eukaryotic cells.

In order to determine the MIC of EIPE-1 on MRSA, a culture of MRSA was grown overnight in Mueller Hinton broth (MHB) at 37° C., sub-cultured by a 1/100 dilution into MHB and dispensed into a 96 well culture block (900 µL of diluted culture in each well). To each well either DMSO or a serial dilution of EIPE-1 was added, then the culture was grown for 18 h at 37° C. The next day each well was tested for either growth or inhibition of growth by measuring of the $OD^{600}$ of the resulting culture. It was determined that a MIC of 16 µg/mL (17 µM) was needed in broth culture to inhibit MRSA growth (data not shown). This data correlates with the zone sizes seen in the Kirby-Bauer disc assay (FIG. 2A). For comparison, the MIC of EIPE-1 was also determined against E. faecalis (8 µg/mL, 9 µM), confirming activity against Gram-positive bacteria.

Figure 3B:
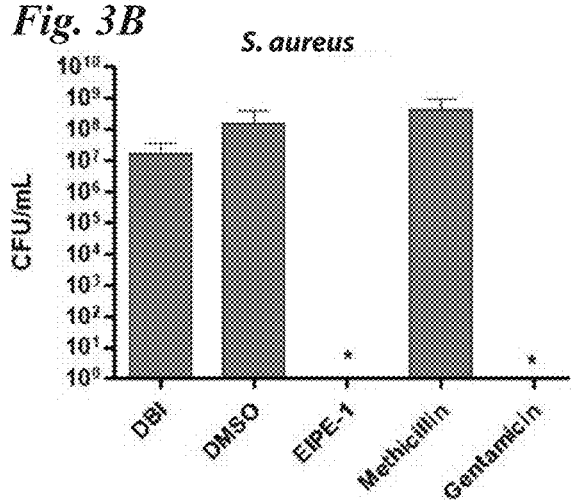
Figure 3C:
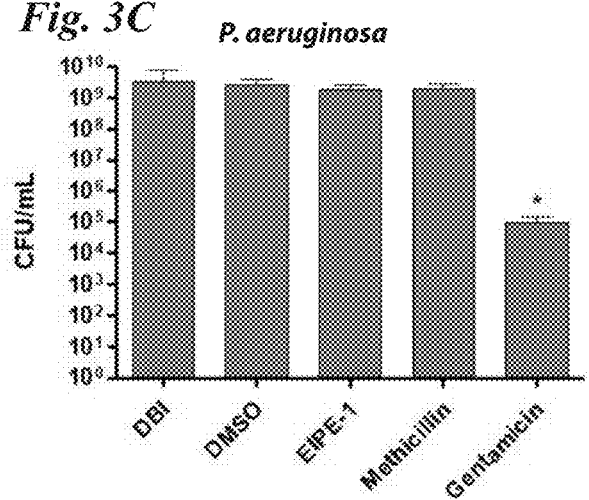

EIPE-1 antimicrobial activity against MRSA and PA was compared to that of Methicillin and Gentamicin treatment. Bacterial cultures were grown, normalized and then exposed to either DBI, DMSO (solvent control), EIPE-1, Methicillin or Gentamicin (FIG. 3). EIPE-1 was effective in killing MRSA (FIGS. 3A (top panel) and 3B). This is highly significant and novel as methicillin resistance is a huge problem in hospitals and patient treatment worldwide. EIPE-1 does not appear to have activity against PA (FIGS. 3A (bottom panel) and 3C). Gram-negative bacteria like PA have an outer membrane covered with lipopolysaccharides that protects the bacteria from antibiotics, dyes, and detergents from penetrating the bacterial cell.

Figure 4A:
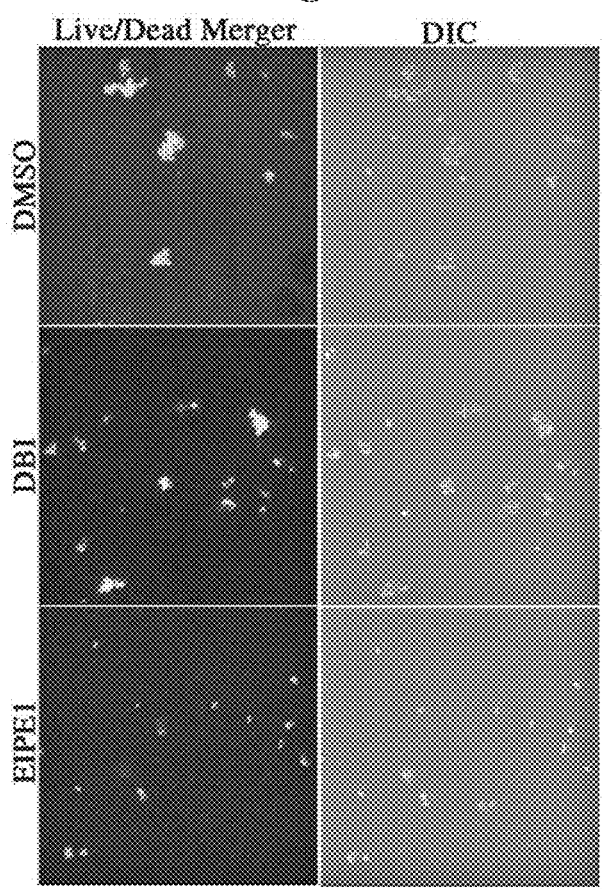
FIG. 4A-C contains a representation of the effects of EIPE-1 on *S. aureus* viability for an embodiment. (A) MRSA viability was assessed after exposure to DMSO, DBI and EPIE-1 for 30 minutes. Live MRSA stain green whereas dead MRSA stain red. DIC images of bacteria are shown in the right panel. (B) Scanning electron microscopy images of DMSO or EIPE-1 treated MRSA. *$p \leq 0.0001$, unpaired two-tailed t test. (C) Percentage of live and dead MRSA from 20 microscopy fields of view were calculated.

To address MRSA viability in response to EIPE-1 treatment, a Live/Dead staining and microscopy was utilized. MRSA was treated with either DBI or EIPE-1 (16 µg/mL, 17 µM each) for 30 minutes (DMSO was used as a negative solvent control) and then stained with the dyes, Syto™ 9 and propidium iodide. MRSA has an intact cell membrane which will stain fluorescent green whereas those systems that have damaged cell membranes will stain red. The DMSO treated MRSA only stained green, and the DBI treated MRSA mostly stained green with only an occasional red stained MRSA bacterium (FIG. 4A, left column). This was in marked contrast to the EIPE-1 treated MRSA which only stained red (FIG. 4A, right column).

Figure 4C:
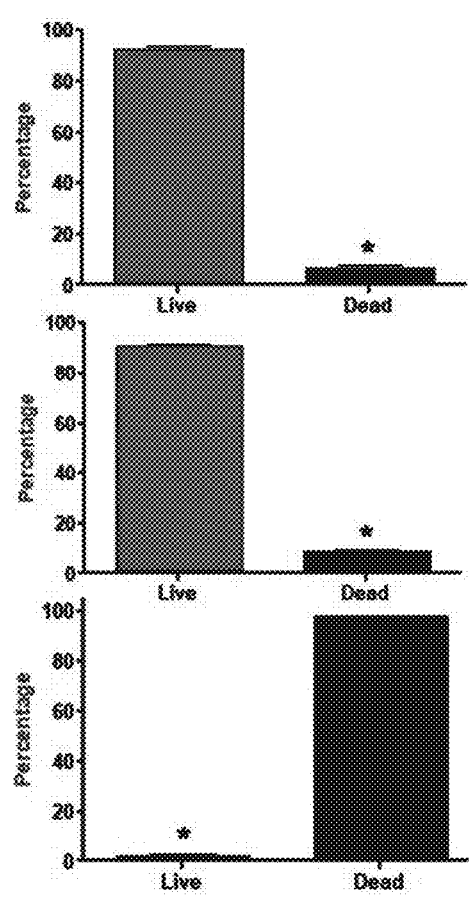
Figure 4B:
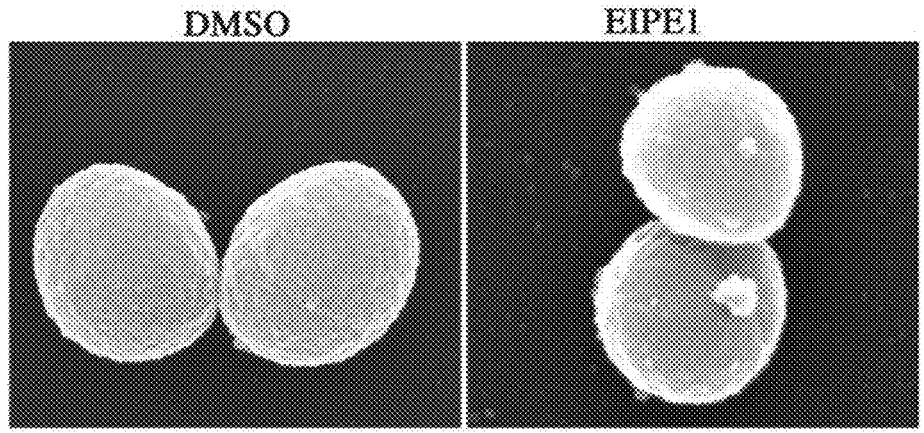

The results show that EIPE-1 indeed killed the MRSA bacteria and suggested that membrane damage was occurring to the MRSA with EIPE-1 treatment. To visualize potential membrane changes, DMSO and EIPE-1 treated MRSA were prepped and visualized by scanning electron microscopy (FIG. 4B). DMSO treated MRSA had intact cell membranes (FIG. 4B; left) whereas the EIPE-1 treated MRSA appeared to have damaged cell membranes as seen via possible protrusions from the MRSA (FIG. 4B; right), confirming that EIPE-1 may affect membrane or bacterial cell wall integrity. FIG. 4(C) contains bar charts that show the percentage of live and dead MRSA from 20 microscopy fields of view.

Example 2

As a further test of an embodiment, the antibacterial properties of EIPE-1 were tested across a large panel of organisms. EIPE-1 was dissolved in DMSO, impregnated onto sterile filter paper disks, and DMSO served as the untreated control according to the following procedure:

1. Prepare a 2.5 μg/μL stock solution of EIPE-1 by micro pipetting 200 μL of DMSO into 2.0 mL Eppendorf Tube containing 0.5 mg of EIPE-1. Dissolve with vortex agitation and store at 4° C.
2. Use forceps to pick up sterile 6.0 mm blank paper disks. Make sure to touch only one side of disc as lightly as possible. While holding blank paper disc, deliver 10.0 μL of the 2.5 μg/μL EIPE-1 solution by touching the micropipette tip to the center of the blank paper disc. Lean the impregnated disc up against the side of a small sterile glass petri dish. Follow same procedure for DMSO control. Allow disks several hours to dry under flowing sterile air.
3. Inoculate starter cultures using cells from working culture cultivated on Mueller-Hinton Agar (MHA; Difco Laboratories). Starters consist of ~20 mL of Mueller-Hinton Broth (MHB; Difco Laboratories) in 125-mL culture flasks. Incubate starter cultures in an Excella E24 Benchtop Incubator Shaker (New Brunswick Scientific Co., Inc., Edison, N.J., USA) at 37° C. and 180 rpm for 15-18 hours.
4. Pour at least 5.0 mL of NMB into 18-mL Kimax tubes. Use a Pasteur pipette to deliver enough of the starter culture cell suspension to reach an optical density ($OD_{620}$) of 0.025 (Spectronic™ 20 optical spectrophotometer; Thermo Electron Corp., Madison, Wis., USA). Ensure that both transmittance and absorbance are set to 0.0 using a blank NMB sample. Incubate in rotary shaking incubator at 37° C. and 180 rpm until optical density reaches 0.1.
5. Deliver 100 μL of test culture to the middle of a small 100 mm×15 mm Petri dish containing ~⅛ in thickness of MHA.
6. Saturate a sterile cotton swab with MHB by dipping the cotton swab into KIMAX® tube with MHB and then touch the swab to the north, south, east, and west side of the KIMAX® tube to remove excess broth.
7. Streak the inoculum as follows:
   a. Start in the center and make four straight lines to the 12, 3, 6, and 9 o'clock position on the petri dish.
   b. Start at the 12 o'clock position and streak side to side all the way down the plate to the 6 o'clock position. Do not leave any gaps between the side to side streaks.
   c. Rotate the petri dish 90° and complete the same side to side streak all the way down the petri dish.
   d. Complete step c. twice more.
   e. Rotate petri dish 45° and complete the side-to-side streak.
   f. Rotate petri dish 90° and complete the side-to-side streak.
8. Use sterile forceps to transfer the DMSO control paper disc onto the agar surface and pat the paper disc down to ensure flush contact. Use the same technique to deliver EIPE-1 paper disc.
9. Place petri dish at 4° C. for 1.0 hour to allow EIPE-1 diffusion in the absence of growth.
10. Incubate petri dish at 37° C. for 18 hours.
11. Observe for zones of growth inhibition surrounding disks. Measure diameter with electronic caliper and subtract 6.0-mm disc diameter.

Results a) Each organism was initially tested once to serve as a screen. If an organism showed susceptibility on the first run, then the run was repeated at least twice.

b) Screening data allowed for following groups to be established.

Group 1: Gram-negative organisms resistant to EIPE-1.
   *Serratia marcescens* ATCC 13880
   *Pseudomonas aeruginosa* ATCC 27853
   *Serratia odorifera* ATCC 53077
   *Escherichia coli* ATCC 25922
   *Escherichia coli* K12413
   *Pasteurella moltocida* P-1581
   *Serratia plymuthica* ATCC 183
   *Serratia rubidaea* ATCC 27593
   *Serratia fonticola* ATCC 9844
   *Serratia entomophila* ATCC 43705
   *Serratia marcescens* CO1-A
   *Serratia marcescens* 8100
   *Serratia marcescens* db11

Group 2: Gram-positive organisms resistant to EIPE-1.
   *Enterococcus faecalis*
   *Micrococcus luteus*
   *Deinoccus radiophilus*
   *Lactococcus lactis*
   *Bacillus cereus*

Group 3: Gram-positive organisms susceptible to EIPE-1.
   *Bacillus subtilis* ATCC 6633
   *Staphylococcus aureus* ATCC 25923
   *Staphylococcus aureus* T-5706
   *Staphylococcus aureus* ATCC 29213
   *Staphylococcus aureus* SFL 8
   *Staphylococcus aureus* SFL 64
   *Staphylococcus epidermidis* c) Significantly, *Bacillus subtilis* ATCC 6633 and *Staphylococcus aureus* ATCC 2592 both exhibited a significantly larger zone of inhibition when exposed to an EIPE-1 potency of 50 μg compared to EIPE-1 potency of 25 μg. Specifically, *Bacillus subtilis* ATCC 6633 exposed to EIPE-1 with potency of 25 g had an inhibition zone diameter of 1.1 mm, whereas the inhibition zone diameter increased to 3.3 mm when the same strain was subjected to EIPE-1 with potency of 50 g. Also, *S. aureus* ATCC 2592 exposed to EIPE-1 with potency of 25 μg had inhibition zone diameter of 1.6 mm, whereas inhibition zone diameter increased to 3.1 mm when this strain was subjected to EIPE-1 with potency of 50 μg. This experimental data suggests a dose response relationship.

Table 1 below contains additional information related to this example:

TABLE 1

Inhibition Zone Diameters

Organism Inhibition Zone Diameter (mm)$^a$ ± SD

| Gram-positive | Cntrl$^b$ | EIPE-1 (25 µg) | Cntrl$^b$ | EIPE-1 (50 µg) | Cntrl$^b$ | EIPE-1 (250 µg) | Cntrl$^b$ | EIPE-HCl (25 µg) |
|---|---|---|---|---|---|---|---|---|
| B. cereus | 0.0 | 0.0 | ND | ND | ND | ND | 0.0 | 0.0 |
| B. subtilis ATCC 6633 | 0.0 | 1.1 ± 0.2 | 0.0 | 3.3 ± 0.1 | 0.0 | 1.8 ± 0.3 | 0.0 | 0.0 |
| L. lactis | 0.0 | 0.4 ± 0.6 | ND | ND | ND | ND | 0.0 | 0.0 |
| M. luteus | 0.0 | 1.0 ± 1.0 | ND | ND | 0.0 | 2.2 ± 1.9 | 0.0 | 0.0 |
| S. aureus ATCC 25923 | 0.0 | 1.6 ± 0.1 | 0.0 | 3.1 ± 0.2 | 0.0 | 2.3 ± 0.2 | 0.0 | 0.0 |
| S. aureus ATCC 29213 | 0.0 | 2.2 ± 0.6 | ND | ND | 0.0 | 2.9 ± 0.3 | 0.0 | 0.0 |
| S. aureus SFL 8 | 0.0 | 2.4 ± 1.3 | ND | ND | 0.0 | 2.4 ± 0.3 | 0.0 | 0.0 |
| S. aureus SFL 64 | 0.0 | 2.5 ± 1.5 | ND | ND | 0.0 | 2.5 ± 0.2 | 0.0 | 0.0 |
| S. aureus T-5706 | 0.6 ± 0.9 | 2.1 ± 0.3 | ND | ND | 0.0 | 2.2 ± 0.2 | 0.0 | 0.0 |
| S. epidermidis | 0.0 | 2.6 ± 0.3 | ND | ND | 0.0 | 3.3 ± 0.5 | 0.0 | 0.0 |

$^a$Diameter of growth inhibition zone minus disk diameter (6.0mm); each value represents the mean of at least three independent determinations.
$^b$Control: DMSO was used to dissolve EIPE-1, therefore control disks were prepared by impregnating with solvent and allowing to air dry prior to plate application.
$^c$ND, not determined.
$^d$Values only represented one independent determination
$^e$Only tested one time Table 2 below shows minimum inhibitory concentration (MIC) and Minimum Bactericidal Concentration (MBC) values for selected bacteria.

TABLE 2

MIC and MBC values.

| Organism | MIC (µg/mL) | MBC (µg/mL) |
|---|---|---|
| S. marcescens ATCC 13880 | 500.000 | 500.000 |
|  | >256 | >256 |
|  | >128 | >128 |
|  | >128 | >128 |
| E. coli ATCC 25922 | 10.420 | 13.021 |
|  | 31.250 | 31.250 |
|  | 128.000 | >265 |
|  | 64.000 | >128 |
|  | 128.000 | >128 |
| P. aeruginosa ATCC 27853 | 250.000 | 500.000 |
|  | 128.000 | >256 |
|  | 64.000 | >128 |
|  | 128.000 | >128 |
| S. typhurans ATCC 14028 | 125.000 | 125.000 |
|  | 7.813 | 15.625 |
|  | 128.000 | >128 |
|  | 128.000 | >128 |
|  | 128.000 | >128 |
| P. moltocida P-1581 | 64.000 | 64.000 |
| S. aureus SFL64 | 0.50 | 4.00 |
|  | 1.000 | 1.000 |
|  | 1.000 | 1.000 |
| S. aureus SFL64 | 0.50 | 4.00 |
|  | 1.000 | 1.000 |
|  | 1.000 | 1.000 |
| S. aureus ATCC 25923 | 2.000 | 2.000 |
|  | 1.000 | 2.000 |
| B. subtilts ATCC 6633 | 1.000 | 1.000 |
| E. faecalis | 1.000 | 1.000 |
|  | 1.000 | 2.000 |
|  | 2.000 | 4.000 |
| S. lactis | 1.000 | 2.000 |
|  | 0.500 | 1.000 |
|  | 0.500 | 2.000 |
| S. epidermidis SK01 | 1.000 | 2.000 |

Conclusions:

EIPE-1 has demonstrated antibacterial properties at a potency of 25 µg according to the data showing B. subtilis, S. aureus (5 disparate strains to include 2 MRSA isolates from CF patients), and S. epidermidis were susceptible. The susceptible organisms are gram-positive, so therefore lack an outer membrane that generally excludes hydrophobic molecules.

The susceptibility of 2 methicillin-resistant Staphylococcus aureus, S. aureus strains (SFL 8 and SFL 64) suggests that EIPE-1 is a novel compound different than the mainstream β-lactam antibiotics.

Since B. subtilis and S. aureus exhibited significantly larger zones when treated with a potency of 50 µg compared to the 25 µg potency the susceptibility is dose dependent.

The disc agar diffusion assay is a qualitative analysis to indicate antibacterial properties and cannot be used to precisely determine the exact degree of susceptibility due to the possibility other factors, including hydrophobicity and poor diffusion properties of the compound may have influenced the sizes of zones.

In summary, a new antimicrobial, EIPE-1, was designed and synthesized, inspired by the black-brown pigment, Eumelanin. It was confirmed that the Eumelanin-inspired core DBI maintained its intrinsic antimicrobial activity, and that enhancement could be achieved with the incorporation of bactericidal moieties. EIPE-1 exhibited biocidal activity against Gram-positive bacteria, including E. faecalis and clinical isolates MRSA with MICs of 8-16 µg/mL (8.5-17 µM). Cell cytotoxicity induced by EIPE-1 was detected at 62.5 µg/mL (66.8 µM) in HeLa cells which was 4-5-fold greater than the MICs. In comparison with Methicillin and Gentamicin treatment, EIPE-1 exhibited biocidal activity against MRSA but did not display any activity against PA or E. coli. Bactericidal effects of EIPE-1 against S. aureus were monitored and confirmed using the Live/Dead staining and fluorescent microscopy. Finally, SEM images of the EIPE-1 exposed MRSA showed membrane damage. These results indicate that this Eumelanin core compound can be used in the preparation of novel antimicrobial compounds.

Example 3. Activity Against Fungal Pathogens

*Cryptococcus neoformans* and *Candida albicans* are opportunistic fungal pathogens that cause infections in immune compromised individuals. *C. neoformans* infects patients with T cell immune deficiencies, such as AIDS patients, transplant patients on immune suppressive drugs, and chemotherapy patients. *C. neoformans* infection can lead to meningitis, which has a 40% fatality rate, even with antifungal treatment. Current estimates in AIDS patients show that 220,000 cases of cryptococcal meningitis occur world-wide each year, with 180,000 yearly deaths. In immune compromised individuals such as hospitalized patients with central venous catheters, *Candida* species can lead to bloodstream infections, which have a 30% fatality rate, even with antifungal treatment. *Candida* is now the 4th leading cause of bloodstream infections in the US, with 46,000 cases per year in the US alone. Despite many advances in antifungal therapies, the currently available antifungal drugs have high toxicity, and fungal organisms have started to acquire resistance to the current antifungal drugs. As a result, there are few options available to assist in the management of life-threatening fungal infections, especially in immunocompromised individuals. Therefore, discovery of novel antifungal therapies is critical for fighting these deadly fungal infections. To combat this issue, an exemplary eumelanin inspired compound, EIPE-1, derived from vanillin was synthesized. The synthetic compound was tested against drug-resistant bacteria, and it has demonstrated antimicrobial effects on methicillin resistant *S. aureus* (MSRA), but not on gram-negative organisms. In this study, we determined the activity of EIPE-1 against the fungal pathogens *Cryptococcus neoformans* and *Candida albicans*.

Reagents.

YPD media, used in the culturing of *C. neoformans* and *C. albicans* cells, was obtained from Fisher Scientific. Phosphate buffered saline (PBS) was purchased at a 10× concentration from Fisher Scientific and was used for washing cryptococcal cells and was diluted 1:10 with deionized water. The solution was then autoclaved to ensure proper sterilization. The plastic ware was purchased from Fisher Scientific. RPMI with MOPS media, used in the MIC Assay, was purchased from Fisher scientific, diluted to a concentration of 0.165 M. Amphotericin B was purchased and reconstituted to a 5 mg/μL concentration.

*Cryptococcus* and *Candida* Cultures.

*Cryptococcus neoformans* serotype A strain H99 as well as *Candida* ablicans strain SC5314, were readily available in the lab. The stock of cells is stored at −80° C. to preserve the fungi and prevent contamination. The cells were grown and maintained in yeast extract-peptone-dextrose (YPD) media (Difco). *Cryptococcus* or *Candida* cells were incubated in YPD broth for 18 hrs at 30° C., in a shaking incubator. After the incubation period, they were washed three times in sterile phosphate-buffered saline (PBS) to remove all remaining residue of YPD. The cells were then quantified by using trypan blue dye exclusion in a hemocytometer.

Incubation of *Cryptococcus* with Amphotericin B or EIPE-1.

*C. neoformans* were suspended in RPMI with MOPS, 0.165M, at a concentration of $0.5 \times 10^3$ cells/mL. RPMI MOPS media was added to a 96-well plate in a volume of 100 μL to every well, with the exception of column 1. An additional 80 μL of RPMI MOPS was added to column 4 for a total of 180 μL/per well. Amphotericin B or EIPE-1 was added to columns 2 and 4 with a volume of 20 μL at a concentration of 1 mg/mL. Contents were mixed, then serially diluted 100 μL down the plate until column 11. The last 100 μL was discarded, leaving column 12 blank. *C. neoformans* was added at a volume of 100 μL per well from column 4 to column 12, so the final volume of the wells was 200 μL. Plates were incubated at 35° C. in a humid incubator for 48 hrs.

Incubation of *Candida albicans* with EIPE-1.

*C. albicans* were suspended in RPMI with MOPS, 0.165M, at a concentration of $0.5 \times 10^3$ cells/mL. RPMI Mops media was added to a 96-well plate in a volume of 100 μL to every well, with the exception of column 1. An additional 80 μL of RPMI MOPS was added to column 4 for a total of 180 μL/per well. EIPE-1 was added to columns 2 and 4 with a volume of 20 μL at a concentration of 1 mg/mL. Contents were mixed, then serially diluted 100 μL down the plate until column 11. The last 100 μL was discarded, leaving column 12 blank. *C. albicans* was added at a volume of 100 μL per well from column 4 to column 12, so the final volume of the wells was 200 μL. Plates were incubated at 35° C. in a humid incubator for 48 hrs.

Data Analysis.

Data analysis was conducted using GraphPad Prism® version 5.00 for Windows. Depending on the data collected and interaction observed between the *Cryptococcus* or *Candida* and the compounds, the one-way ANOVA with the Tukey's multiple comparison test was used to compare the data.

Tables 3 and 4 contain exemplary mean MIC values for EIPE-1 using isolates ranged between 4 μg/mL and 11 Ig/mL for *Candida* clinical samples.

TABLE 3

| Minimum inhibitory concentration (MIC) for the isolate of *C. neoformans* | |
| --- | --- |
| Antifungal | MIC μg mL |
| Amphotericin B | 0.6825 ± 0.2925 |
| EIPE-1 | 1.749 ± 0.1080 |

TABLE 4

| Minimum inhibitory concentration (MIC) for the isolate of *C. albicans* | |
| --- | --- |
| Antifungal | MIC μg/mL |
| Amphotericin B | 0.5606 ± 0.1219 |
| EIPE-1 | 2.705 ± 0.3962 |

*C. neoformans* minimum inhibitory concentration average was 0.6 μg/mL with Amphotericin B across four experiments. With EIPE-1, the MIC for the organism was 1.67 g/mL across seven MIC assays, which is more than double of Amp B. Candida MIC is 0.5606 g/ml for Amp B for two experiments and MIC of 2.46 µg/mL for the compound EIPE-1 across seven experiments.

FIG. 6 contains optical density measurements for EIPE-1 and Amphotericin B drug inhibition of C. neoformans and C. albicans. As can be seen, each drug displays lower optical densities at 3.625 µg/mL concentrations. However, ODs vary considerably after this concentration in all 18 experiments with fungal organisms exposed to EIPE-1 displaying the most variability in ODs.

Cell Fixation of Cryptococcus.

C. neoformans were suspended in RPMI with MOPs, 0.165M, at a concentration of $2.0\times10^6$ cells/mL. RPMI Mops media was added to a 2 mL collection tube in a volume of 100 µL. EIPE-1 was added to each tube at the minimum inhibitory concentration 1.749 µg/mL at a volume of 100 µL. The tubes were incubated at 35° C. in a humid incubator for set time points of 4 hrs, 8 hrs, 12 hrs, or 24 hrs. Once removed, the tubes were placed in a centrifuge for 1 min. at 5000 rpm. Media was removed. The pellet was resuspended in 2.0% glutaraldehyde in 0.1 M cacodylate buffer at a volume of 1 mL for a minimum of 2 hrs.

SEMs of Cryptococcus.

Fixed C. neoformans cells were placed in a centrifuge for 1 min at 5000 rpm. Media was removed and C. neoformans was rinsed 3 times in a buffered wash at fixed intervals of 15 mins. Rinsed cells were resuspended in 1% $OsO_4$ at room temperature for 1 hr in a 36-well plate with a cover slip. 1% $OsO_4$ was removed. C. neoformans was rinsed 3 times in a buffered wash at fixed intervals of 15 mins. C. neoformans were dehydrated in ethanol at 50%, 70%, 90%, 95%, and 100% three times at fixed intervals of 15 mins. C. neoformans were wash two times with hexamethyldisilane at a time interval of 5 mins. Cover slips were placed on a clear sheet for 12 hrs to dry. Cover slips were mounted on stubs with silver paint. The cover slips were covered in an Au—Pd coat.

SEM Imagery

Imagery was taken with a FEI Quanta 600 field-emission gun Environmental Scanning Electron Microscope with a Bruker EDS X-ray microanalysis system and HKL EBSD system. The results are presented in FIG. 7. As can be seen, when C. neoformans was exposed to the EIPE-1 at the minimum inhibitory concentration for various time intervals, the compound affected the fungal cells early with changes to the cell wall shown at 4 hours. After prolonged exposure, the yeast cells began to display a release of internal organs and/or possibly deformed budding cells.

In summary, an exemplary Melanin-inspired antimicrobial (EIPE-1) was tested against the following fungal organisms: Candida albicans (lab strain SC5314) and Cryptococcus neoformans (lab strain H99). EIPE-1 minimal inhibitory concentrations (MIC) for Candida albicans and Cryptococcus neoformans were 4.7 µg/mL and 3.1 µg/mL, respectively. These MIC values are similar to those found with currently available antifungal drugs.

Example 4. Additional Studies with Candida

EIPE-1 was evaluated against multiple Candida isolates from the airways of CF patients. As shown in FIG. 8, mean MIC values for EIPE-1 using these isolates ranged between 4 g/mL and 11 µg/mL.

Example 5. Synthesis of EIPE-2HD

Scheme 2 below shows the synthetic route for the compound 3,3'-((((5,6-dimethoxy-2-(2-hexyldecyloxoxycarbonyl)-1-methyl-1H-indole-4,7-diyl)bis(ethyne-2,1-diyl))bis(4,1-phenylene))bis(oxy))bis(N,N,N-trimethylpropan-1-aminium) iodide (EIPE-2HD).

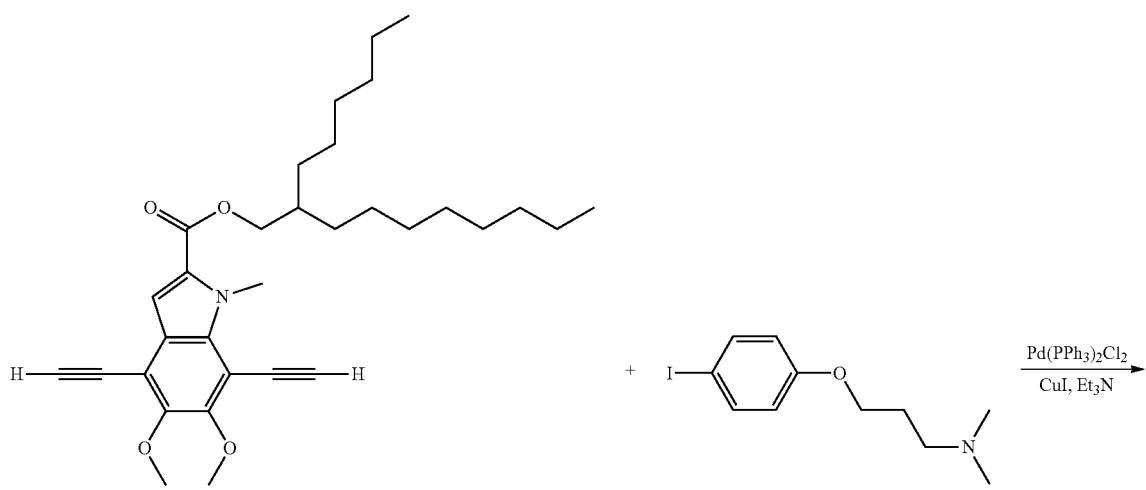

-continued

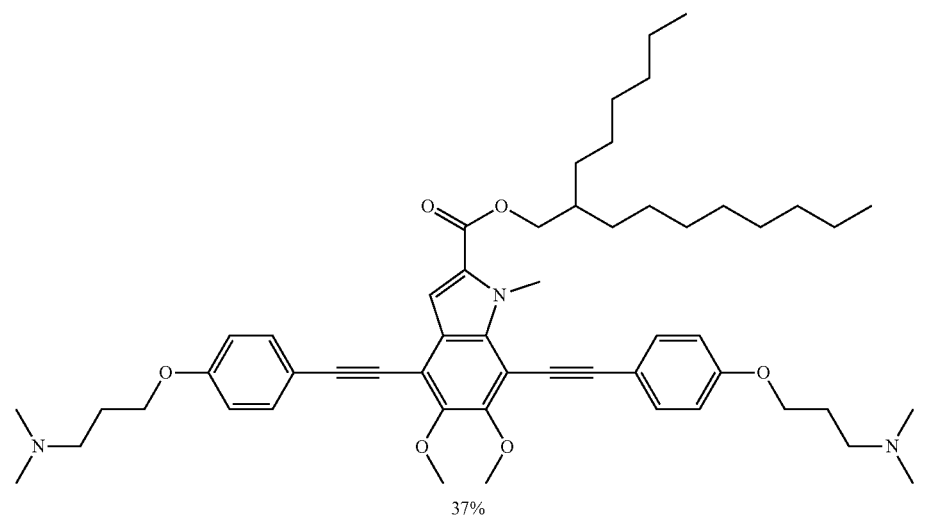

37%

$$\downarrow \begin{array}{c} CH_3I \\ EtOAC \end{array}$$

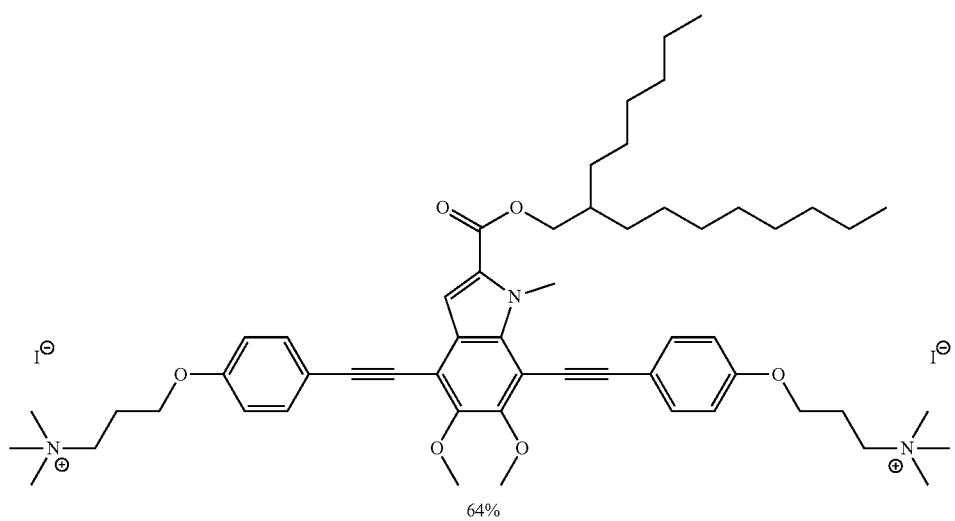

64%

Thus, the present invention is well adapted to carry out the objects and attain the ends and advantages mentioned above as well as those inherent therein. While the inventive device has been described and illustrated herein by reference to certain preferred embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

What is claimed is:

1. A melanin-based antimicrobial of Formula I:

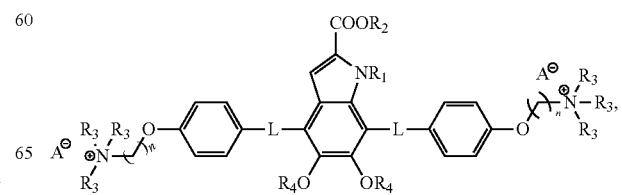

Formula I wherein
- R1, R2, R3, and R4 are independently the same or different and are alkyl, alkenyl, alkynyl, cycloalkyl, aryl, perfluoroalkyl, a heterocyclic amine or a quaternary ammonium salt;
- L is a linker comprising 1-6 carbon atoms;
- A is a halogen, a carboxylic acid anion or an inorganic anion; and
- n=1-10.

2. The melanin-based antimicrobial of claim 1, wherein L is

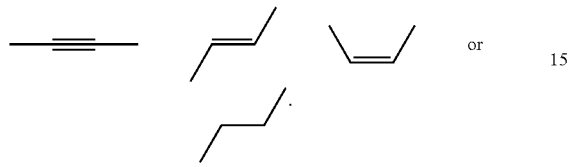

3. The melanin-based antimicrobial of claim 1, having a formula:

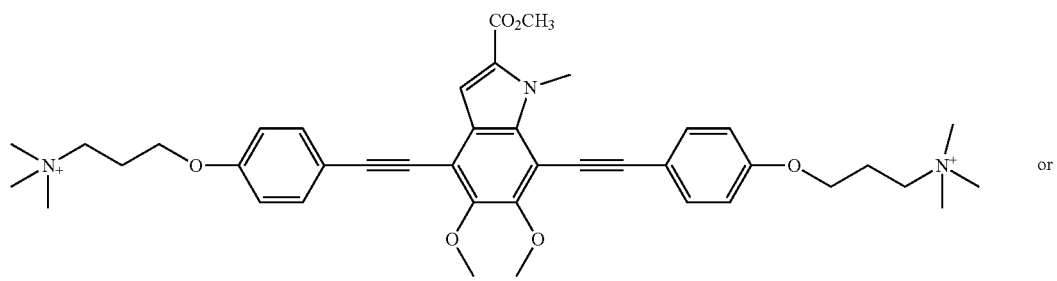 or

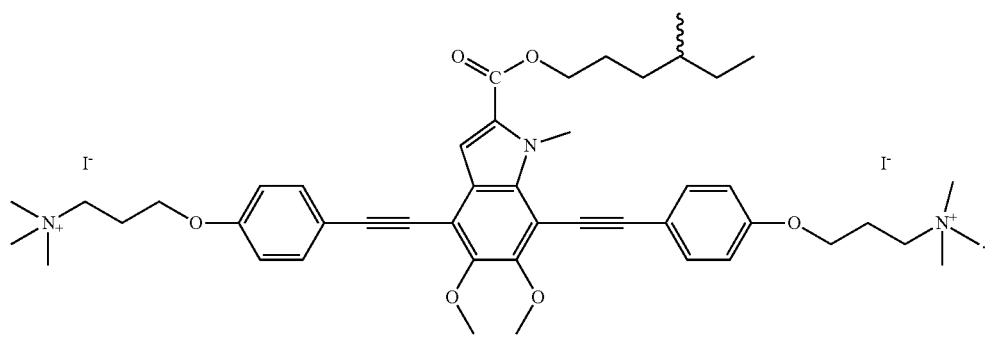

4. The melanin-based antimicrobial of claim 1, which is present in a composition comprising at least one carrier.

5. The melanin-based antimicrobial of claim 4, wherein the composition is a pharmaceutical composition, and the carrier is a pharmaceutically acceptable carrier.

6. The melanin-based antimicrobial of claim 5, wherein the pharmaceutical composition is formulated for intravenous, oral or topical administration.

7. The melanin-based antimicrobial of claim 4, wherein the composition is formulated as a spray, foam or wash for disinfecting surfaces, containers and equipment.

8. A method of treating a microbial infection in a subject in need thereof, comprising administering to the subject a therapeutically effective amount of a compound of claim 1.

9. The method of claim 8, wherein the microbial infection is caused by a bacteria.

10. The method of claim 9, wherein the bacteria is a drug-resistant bacteria.

11. The method of claim 9, wherein the bacteria is a Gram positive bacteria and the compound is

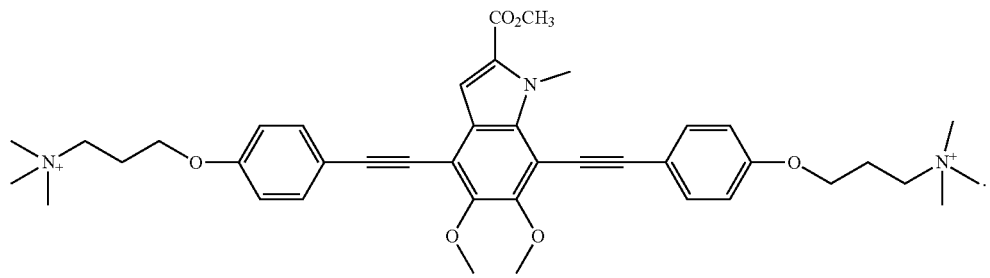

12. The method of claim 9, wherein the Gram positive bacteria is *Bacillus subtilis, Staphylococcus aureus, Staphylococcus epidermidis* or *Enterococcus faecalis.*

13. The method of claim 12, wherein the *Staphylococcus aureus* is methicillin resistant *S. aureus* (MRSA).

14. The method of claim 8, wherein the microbial infection is caused by a fungus.

15. The method of claim 14, wherein the fungus is a drug-resistant fungus.

16. The method of claim 14, wherein the fungus is *Candida albicans* or *Cryptococcus neoformans.*

17. The method of claim 14, wherein the compound is

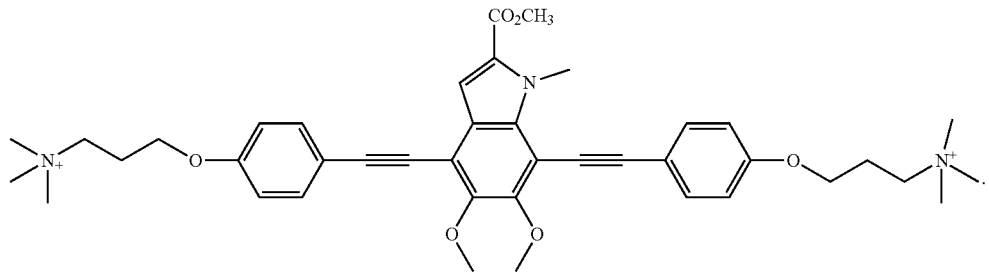

18. The method of claim 8, wherein the subject is immunocompromised or immunosuppressed.

19. A method of killing or damaging a microbe, comprising,
contacting the microbe with at least one compound of claim 1.

* * * * *